US005414091A

United States Patent [19]

Chinoporos et al.

[11] Patent Number: 5,414,091

[45] Date of Patent: May 9, 1995

[54] DYE-PROVIDING COMPOUNDS

[75] Inventors: Efthimios Chinoporos, Cambridge; Robert H. Pauze, Middleboro; David P. Waller, Lexington; David C. Whritenour, Franklin, all of Mass.

[73] Assignee: Polaroid Corporation, Cambridge, Mass.

[21] Appl. No.: 247,877

[22] Filed: May 23, 1994

Related U.S. Application Data

[60] Division of Ser. No. 58,494, May 6, 1993, Pat. No. 5,340,689, which is a continuation-in-part of Ser. No. 923,843, Jul. 31, 1992, Pat. No. 5,316,887.

[51] Int. Cl.$^6$ .................. C07D 277/60; C07D 249/08; C08F 28/06

[52] U.S. Cl. .................................. 548/214; 548/262.4; 548/149; 526/257

[58] Field of Search ...................... 548/149, 214, 262.4; 526/257

[56] References Cited

U.S. PATENT DOCUMENTS

| | | | |
|---|---|---|---|
| 3,719,489 | 3/1973 | Cieciuch et al. | 96/29 |
| 4,053,312 | 10/1977 | Fleckenstein | 96/3 |
| 4,098,783 | 7/1978 | Cieciuch et al. | 260/147 |

FOREIGN PATENT DOCUMENTS

| | | |
|---|---|---|
| 0073245 | 3/1982 | European Pat. Off. . |
| 0082506 | 12/1982 | European Pat. Off. . |
| 0495406 | 1/1992 | European Pat. Off. . |
| 2284140 | 9/1975 | France . |
| 59-180548 | 10/1984 | Japan . |

*Primary Examiner*—Joseph L. Schofer
*Assistant Examiner*—Wu C. Cheng
*Attorney, Agent, or Firm*—Edward W. Black

[57] ABSTRACT

There are disclosed dye-providing compounds comprising color coupler dyes substituted on the phenylene diamine portion with one or two cyclic 1,3-sulfur-nitrogen groups. The dye-providing compounds are capable of releasing the coupler dye upon cleavage in the presence of silver ions or a soluble silver complex. The dye-providing compounds are useful as image-forming materials in color thermographic, photothermographic and other photographic processes.

12 Claims, 1 Drawing Sheet

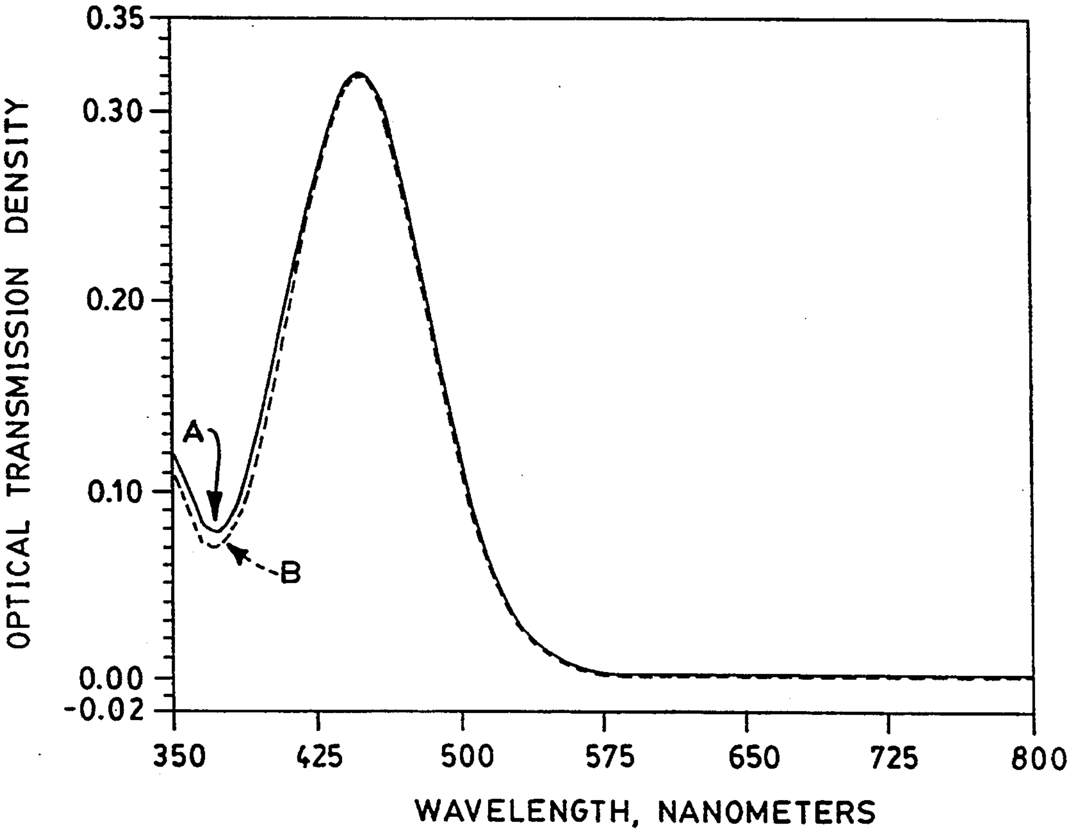
0.35
0.30
0.20
0.10
0.00
-0.02
OPTICAL TRANSMISSION DENSITY
A
B
350
425
500
575
650
725
800
WAVELENGTH, NANOMETERS

DYE-PROVIDING COMPOUNDS

CROSS REFERENCE TO RELATED APPLICATIONS

This application is a divisional of U.S. patent application Ser. No. 08/058,494, filed May 6, 1993, now U.S. Pat. No. 5,340,689, which is a continuation-in-part of application Ser. No. 07/923,843, filed Jul. 31, 1992, now U.S. Pat. No. 5,316,887.

BACKGROUND OF THE INVENTION

1. Field of the Invention

This invention relates to image-forming materials, specifically to dye-providing compounds which, in the presence of silver ions and/or a soluble silver complex, undergo a cleavage reaction to liberate a diffusible coupler dye.

2. Description of the Related Art

U.S. Pat. No. 3,719,489 discloses silver ion assisted cleavage reactions useful in photographic systems. As disclosed therein, photographically inert compounds are capable of undergoing cleavage in the presence of silver ions made available imagewise during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color-providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Color-providing compounds useful in the above process form the subject matter of U.S. Pat. No. 4,098,783, a continuation in part of said U.S. Pat. No. 3,719,489. The color-providing compounds disclosed therein may comprise one or more dye radicals and one or more 1,3-sulfur-nitrogen moieties. For example, they may comprise one complete dye or dye intermediate and one cyclic 1,3-sulfur-nitrogen moiety. Alternatively, the color-providing compounds may comprise two or more cyclic moieties for each dye radical or dye intermediate and vice versa. Particularly useful dye-providing compounds disclosed therein comprise a dye containing from 1 to 4 and preferably 1 or 2 cyclic 1,3-sulfur-nitrogen groups and may be represented by the formula $$D-[(L)_{m-1}-Y]_n \qquad (A)$$

wherein D represents a dye radical, i.e., the radical of an organic dye possessing at least one carbon atom, L is a divalent organic linking group containing at least one carbon atom, m is a positive integer 1 or 2, n is a positive integer from 1 to 4, and Y is a cyclic 1,3-sulfur-nitrogen group. Indophenol, indoaniline, and azomethine dyes are broadly disclosed therein as useful dye radicals, although no specific examples are given.

European Patent No. 0 073 245 describes certain polymers, among others, which comprise recurring units containing cyclic 1,3-sulfur-nitrogen groups of the type disclosed in the aforementioned U.S. Pat. No. 4,098,783. These polymeric cyclic 1,3-sulfur-nitrogen compounds are capable of undergoing cleavage in the presence of an imagewise distribution of silver ions or a silver complex to release a photographically useful group, e.g., an image dye-providing material, corresponding to said imagewise distribution.

Japanese Kokai 59-180548 having a Laid-Open date of Oct. 13, 1984 discloses a heat-developable silver halide photosensitive imaging system wherein the dye-providing material contains a heterocyclic ring containing a nitrogen atom and a sulfur or selenium atom which heterocyclic ring is subject to cleavage in the presence of silver ions to release a diffusible dye. An example of a suitable dye-providing material is a thiazolidine dye such as disclosed in the aforementioned U.S. Pat. No. 4,098,783. The process involves imagewise exposing the photosensitive system to light and subsequently or simultaneously heating the photosensitive system under a substantially water-free condition, in the presence of a base or base precursor, whereby an oxidation-reduction reaction between the exposed photosensitive silver halide and a reducing agent occurs. In the exposed areas a negative silver image is formed. In the unexposed areas, the silver ion, present in inverse proportion to the silver image, causes the heterocyclic ring of the dye-providing material to be cleaved releasing a diffusible dye. The diffusible dye is then transferred to an image-receiving layer whereby a positive dye image is formed.

Useful dye radicals to be used in the dye-providing materials for photographic and particularly for photothermographic applications, are coupler dyes, i.e., dyes formed by the oxidative coupling of a phenylene diamine with a color coupler, e.g., azomethine, indoaniline, indamine, and indophenol dyes, as disclosed in the copending U.S. patent application, Ser. No. 07/923,843 of M. Arnost et al filed Jul. 31, 1992. Coupler dyes are well-known dyes having desirable hues for color reproduction. However, modification of these known coupler dyes to incorporate cyclic 1,3-sulfur-nitrogen moieties can undesirably influence their color characteristics by shifting the absorption of the starting coupler dye.

It has now been found that by substituting the developer portion of known coupler dyes in a particular manner with aldehyde or ketone functionalities, those functionalities being necessary to prepare the cyclic 1,3-sulfur-nitrogen dye-providing compounds, the chromophores of the resulting aldehyde and ketone coupler dyes are virtually unchanged. In addition, the aldehyde and ketone substituted coupler dyes and the dye-providing compounds produced therefrom are readily synthesized.

SUMMARY OF THE INVENTION

The present invention provides dye-providing compounds represented by Formula I

Formula I

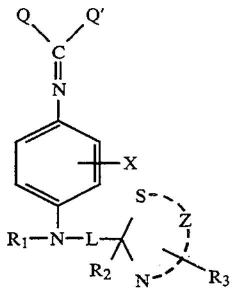

(a)

or

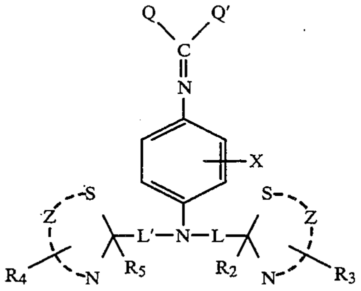

(b)

wherein:

Q, Q′ and C taken together represent a dye-forming coupler moiety wherein C is the coupling carbon of said coupler moiety;

X is selected from hydrogen, branched or unbranched alkyl, substituted alkyl (e.g. aralkyl, thioalkyl such as thionethyl), alkoxy, aryl, alkaryl, carboxy, amido, sulfamyl, sulfonamido, halo e.g. fluoro and chloro, nitro, cyano and preferably X is positioned on the phenyl ring ortho to the coupling nitrogen;

$R_1$ is selected from hydrogen, branched or unbranched alkyl, substituted alkyl (e.g. aralkyl, hydroxy substituted alkyl, sulfonamido substituted alkyl), cycloalkyl, aryl, alkaryl, and alkoxy, or $R_1$ together with $R_2$ represents the atoms necessary to complete a 5, 6 or 7-membered heterocyclic ring with N and L. $R_1$ is preferably lower alkyl containing 1 to 6 carbon atoms, e.g., ethyl;

$R_2$ and $R_5$, the same or different, represent hydrogen, a monovalent organic radical or together with L or L′ represent the atoms necessary to complete a spiro union with one of the cyclic 1,3-sulfur-nitrogen moieties, or $R_2$ together with $R_5$ represents the atoms necessary to complete a 5, 6 or 7-membered heterocyclic ring with L′, N and L;

$R_3$ and $R_4$, the same or different, represent ballast groups which render the dye-providing compound substantially immobile and nondiffusible in the imaging media;

L and L′ represent divalent organic linking groups, the same or different, each containing at least two carbon atoms, provided that when one of L and L′ contains 2 carbon atoms, the other contains at least 3 carbon atoms; and, Z and Z′, the same or different, represent the carbon atoms necessary to complete an unsubstituted or substituted 5- or 6-membered heterocyclic ring system;

The present invention also provides coupler dyes which are released upon the silver ion assisted cleavage of the above described dye-providing compounds.

The present invention further provides photographic, photothermographic and thermographic diffusion transfer image-recording materials using the above described dye-providing compounds.

Other objects of the invention will in part be obvious and will in part appear hereinafter.

The invention accordingly comprises the processes involving the several steps and relation and order of one or more of such steps with respect to each of the others, and the product and compositions possessing the features, properties and relation of elements which are exemplified in the following detailed disclosure, and the scope of the application of which will be indicated in the claims.

For a fuller understanding of the nature and objects of the invention, reference should be had to the following detailed description.

BRIEF DESCRIPTION OF THE DRAWING

The FIGURE is a graphic illustration of the spectral absorption characteristics of an aldehyde substituted coupler dye according to the present invention and also the spectral absorption characteristics of an analogous coupler dye without the aldehyde substitution.

DETAILED DESCRIPTION OF THE INVENTION

It is well known in the photographic art that oxidized color developers react with dye-forming couplers to form a wide variety of colors. The dye-forming coupler moieties of the present invention represented by Q, Q′ and C in Formula I may be any of those coupler moieties known in the art to form a colored reaction product with an oxidized color developer. Q and Q′ represent the groups attached to the coupling carbon C, necessary to complete the dye-forming coupler moiety. Q and Q′ may be independent of each other or taken together may form a ring system to complete the dye-forming coupler moiety.

Examples of coupler moieties that may be used for forming yellow dyes are those derived from acylacetanilides such as benzoylacetanilides and particularly pivaloylacetanilides and variations of pivaloylacetanilides. Coupler moieties that may be used for forming magenta dyes are those derived from pyrazolotriazoles, indazolones, pyrazolobenzimidazoles, and particularly, pyrazolones such as 1-aryl-5-pyrazolones. Coupler moieties that may be used for forming cyan dyes are those derived from substituted phenols or substituted naphthols, particularly 2-carbonamidophenols and 1-hydroxy-2-naphthamides.

As noted above, the formation of image dyes by the oxidative coupling reaction between a color-forming coupler and a color developer in color photographic processes is well known, and a review of these color-forming reactions and color couplers useful therein can be found in, e.g., James, T. H., *The Theory of the Photographic Process,* fourth ed., MacMillan Publishing Co., Inc., New York, 1977, pp. 335–362 and *The Chemistry of synthetic Dyes,* vol. iv, J. Bailey and L. A Williams, "The Photographic Color Development Process", pp. 341–387, Academic Press, New York, 1971.

Illustrative coupler moieties which may be used for the yellow dye-providing compounds of the present invention include those couplers having the structural formula

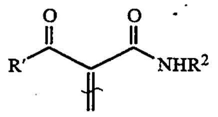

wherein "╫" indicates the point of attachment of the coupler moiety to the coupling N of the phenylene diamine moiety and wherein $R^1$ is selected from $(CH_3)_3C—$, $CH_3OCH_2(CH_3)_2C—$, $C_6H_5O(CH_3)_2C—$ and phenyl, unsubstituted or substituted with one or more groups selected from alkyl, alkoxy, nitro, halo such as chloro, and carbonamido; $R^2$ is phenyl, unsubstituted or substituted with one or more groups selected from alkyl, alkoxy, nitro, halo such as chloro, and carbonamido, said phenyl group $R^2$ being the same or different from said phenyl group $R^1$.

Illustrative dye-forming coupler moieties which may be used for the magenta dye-providing compounds of the present invention include

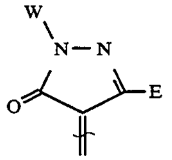

wherein "╫" indicates the point of attachment of the coupler moiety to the coupling N of the phenylene diamine moiety and W is selected from benzimidazolyl and phenyl, unsubstituted or substituted with one or more groups selected from alkyl, alkoxy, amino, amino substituted with phenyl or substituted with one or two alkyl groups and halo such as chloro; and, E is selected from alkyl, aryl usually phenyl, amino, amino substituted with phenyl or substituted with one or two alkyl groups, heterocyclic amino, carbonamido, sulfonamido, guanidino and ureido. Particularly useful magenta couplers are those described in Japanese Kokai 01-90403 having a Laid-Open date of Apr. 6, 1989.

Illustrative coupler moieties for the cyan dye-forming compounds are represented by

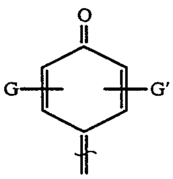 and 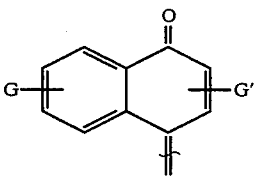

wherein "╫" indicates the point of attachment of the coupler moiety to the coupling N of the phenylene diamine moiety and G is selected from hydrogen, alkyl, alkoxy, halo such as chloro and carbonamido; G' is selected from hydrogen, carbonamido, perfluoroacylamido, ureido and carbamyl. In the phenol derivatives, G' is usually 2-carbonamido ($—NHCOR^3$) and in the naphthol derivatives, G' is usually 2-carbamyl ($—CONR_4R^5$) wherein $R^3$ typically is alkyl substituted with phenoxy and $R^4$ and $R^5$, the same or different, typically are selected from hydrogen, alkyl, phenyl, p-alkoxyphenyl, p-chlorophenyl, p-nitrophenyl and p-sulfamylphenyl. Particularly useful cyan couplers are those described in Japanese Kokai 02-265792 having a Laid-Open date of Oct. 30, 1990.

The choice of color coupler moiety to be used in the present invention is primarily limited by the spectral characteristics it is desired to have in the dye product comprising the color coupler and the dye-developer provided, of course, the released coupler dye is capable of diffusing to the image receiving layer.

The divalent hydrocarbon radicals, L and L' in Formula I, refer to chemical linkages joining the coupler dye to the cyclic 1,3-sulfur-nitrogen moiety. The chemical linkage is chosen so that it insulates the cyclic 1,3-sulfur-nitrogen moiety from the coupler dye. Thus, once the dye-providing compounds are cleaved in the presence of silver ions to release the diffusible coupler dye containing the aldehyde and/or ketone group(s) formed upon cleavage of the cyclic 1,3-sulfur-nitrogen moiety(ies), the aldehyde and/or ketone group(s) have no substantial influence on the chromophoric characteristics of the coupler dye. Examples of suitable divalent hydrocarbon radicals include alkylene groups, e.g., $(—CH_2—)_3$, $(—CH_2—)_4$, cycloalkylene groups, aralkylene groups, e.g., $—CH_2—Ar—$ wherein Ar represents arylene and alkarylene groups, e.g., $—CH_2—Ph—CH_2—$ where Ph represents a substituted or unsubstituted phenyl ring. Preferred divalent hydrocarbon radicals are the alkylene radicals possessing 2 to 8 carbon atoms, provided that for those compounds represented by (b) in Formula I when one of L and L' contains 2 carbon atoms, the other contains at least 3 carbon atoms; otherwise, the aldehyde or ketone coupler dye used to make the dye-providing compound tends to be unstable on standing. As the number of carbon atoms increases, the molecular weight of the released dye increases, and this may reduce the diffusibility of the released dye.

Z and Z' in Formula I, as stated above, represent the atoms necessary to complete either a substituted or unsubstituted 5- or 6-membered heterocyclic ring. Preferably, the cyclic groups are a thiazolidine (II) or benzothiazolidine (III), represented by the formulae below

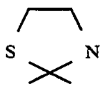

Formula II

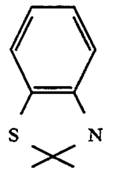

Formula III wherein the above formulae are intended to also include the corresponding substituted thiazolidines and benzothiazolidines.

$R_1$ can be any of those groups known in the photographic art to be substituted on the amino portion of phenylene diamine color developers such as those described in the aforementioned James, T. H., *The Theory of the Photographic Process,* fourth ed., MacMillan Publishing Co., Inc., New York, 1977, pp. 335-362 and *The Chemistry of Synthetic Dyes,* vol. iv, J. Bailey and L. A.

Williams, "The Photographic Color Development Process", pp. 341–387, Academic Press, New York, 1971. $R_1$ is generally selected from hydrogen, branched or unbranched alkyl, substituted alkyl (e.g. aralkyl, hydroxy substituted alkyl, sulfonamido substituted alkyl), cycloalkyl, aryl, alkaryl, and alkoxy and is preferably lower alkyl containing 1 to 6 carbon atoms, e.g., ethyl, or $R_1$ together with $R_2$ represents the atoms necessary to complete a 5, 6 or 7-membered heterocyclic ring with N and L;

$R_2$ and $R_5$, the same or different, represent hydrogen, a monovalent organic radical or together with L or L′ represent the atoms necessary to complete a spiro union with one of the cyclic 1,3-sulfur-nitrogen moieties, or $R_2$ together with $R_5$ represents the atoms necessary to complete a 5, 6 or 7-membered heterocyclic ring with L′, N and L.

The function of the ballast groups, $R_3$ and $R_4$ in Figure I, is to insolubilize or immobilize the dye-providing compounds to render them substantially non-diffusible during processing. The ballast groups, $R_3$ and $R_4$, may be substituted on the carbon atoms represented by Z and Z′ or on the N atom of the 1,3-sulfur-nitrogen moiety, or rather than representing a single ballast group, $R_3$ and $R_4$ may each represent two or more groups substituted on the 1,3-sulfur-nitrogen moiety which together immobilize or insolubilize the compound. Preferably, $R_3$ and $R_4$ each represent a single ballast group substituted on the N atom of the 1,3-sulfur-nitrogen cyclic moiety.

The selection of a particular ballast group will depend primarily on whether it is desired to employ only one ballast group or to employ two or more groups capable of insolubilizing or immobilizing the compound. Where two or more groups are employed to render the dye-providing compound substantially non-diffusible, lower alkyl radicals may be used. Where only one group is used for ballasting, it is more effective to employ, for example, a higher alkyl radical, such as decyl, dodecyl, lauryl, stearyl, and oleyl or a carbocyclic or heterocyclic ring having 6 members or more or a polymer residue. Where cyclic compounds are employed, the carbocyclic or heterocyclic ballast group may be bonded to a single atom or to adjacent atoms of the parent molecule and may be bonded to a single atom by a valence bond or through a spiro union.

Where the ballast represents a polymeric residue, the polymeric dye-providing materials of the present invention generally comprise recurring units of the formula

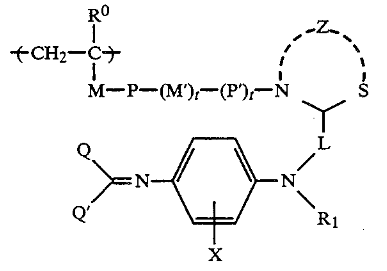

wherein $R^0$ represents hydrogen or lower alkyl usually containing 1 to 6 carbon atoms; M and M′ each represent a divalent linking group, e.g.

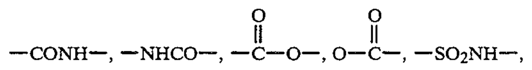

$-NH-CO-NH-$;

P and P′ each represent a divalent hydrocarbon group, containing at least two carbon atoms; t is 0 or 1; and $R_1$, L, Z, X, Q and Q′ are as previously defined.

The polymeric dye-providing materials of the present invention preferably have a weight average molecular weight (Mw) of at least 10,000.

The present invention is concerned with the specific substitution of cyclic 1,3-sulfur-nitrogen moieties on the developer portion of coupler dyes as illustrated by (a) and (b) in Formula I. However, the dye-providing compounds of the present invention may include cyclic 1,3-sulfur-nitrogen moieties in addition to those represented by Formula I, such as dye-providing compounds (xi) and (xii) illustrated hereinafter. It is noted that the aldehyde functionalities present on the coupler moieties of the released coupler dyes (xi) and (xii) shown below do effect the chromophore of the coupler dyes.

As discussed in the aforementioned *The Chemistry of Synthetic Dyes*, Vol. IV, J. Bailey and L. A. Williams, "The Photographic Color Development Process," pp. 341–387, particularly pp. 359–361, Academic Press New York, 1971, the relationship between structure and dye absorption depends on the electrophilicity of the substituents in the coupler moieties of coupler dyes. Electron-withdrawing groups cause bathochromic, and electron-donating groups cause hypsochromic shifts in absorption maxima. Thus, the aldehyde groups on the color couplers of dyes (xi) and (xii) will cause a bathochromic shift in the absorption maxima relative to those analogous dyes without the aldehyde group(s).

The dye-providing compounds of the present invention are useful in photographic imaging systems utilizing silver halide wherein the method of processing employs either wet processing to develop the image such as disclosed in U.S. Pat. No. 4,740,448 issued Apr. 26, 1988 to Peter O. Kliem, and in the aforementioned U.S. Pat. No. 3,719,489 issued Mar. 6, 1973 to Ronald F. W. Cieciuch et al, or thermal processing which develops the image by heating. The thermally processed photographic systems may be those processed in the presence of base or a base-precursor, i.e., a compound which generates a base under the processing conditions, such as those disclosed in the aforementioned Japanese Kokai No. 59-180548, or they may be those processed in the absence of base or a base precursor as described in the aforementioned U.S. patent application, Ser. No. 07/923,843 of Michael J. Arnost et al, filed Jul. 31, 1992.

As mentioned previously, the dye-providing compounds of Formula I are cleaved in the presence of silver ions or a soluble silver complex to release a diffusible coupler dye as depicted in Scheme I.

SCHEME I

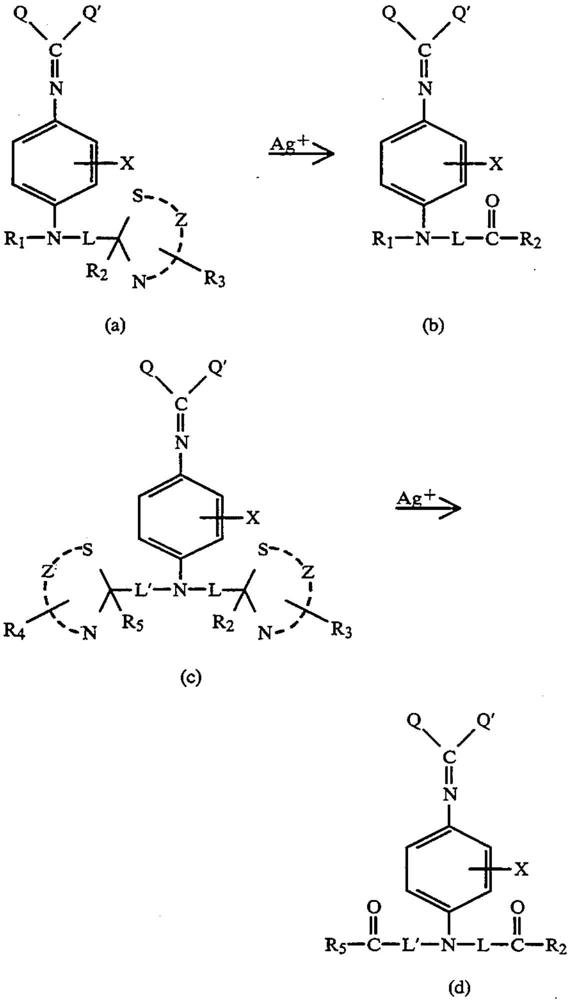

(a) (b) (c) (d)

wherein Q, Q', X, $R_1$, $R_2$, $R_3$, $R_4$, $R_5$, L, L', Z and Z' are as defined above.

In photographic and photothermographic systems, the dye-providing compounds of this invention are capable of releasing a diffusible coupler dye in the presence of the imagewise distribution of silver ions and/or soluble silver salt complex made available during processing of a silver halide emulsion, in an imagewise distribution corresponding to that of the silver ions and/or soluble silver salt complex. The dye-providing compounds are also useful in thermographic imaging systems wherein a source of silver ions or a soluble silver complex becomes available, upon heating in an imagewise manner, to cleave the dye-providing compounds such as described in the U.S. patent application, Ser. No. 07/923,858 of James R. Freedman et al, filed Jul. 31, 1992, now abandoned and the U.S. patent application of James R. Freedman et al, Ser. No. 07/994,898, filed Dec. 22, 1992, now abandoned.

As mentioned above, substitution of a coupler dye with the necessary aldehyde or ketone moiety(ies) and any necessary linking group(s) according to the present invention has substantially no influence on the color characteristics of the starting coupler dye. Thus, a particular coupler dye can be selected for use according to the present invention without the worry that the modification necessary to make the 1,3-cyclic sulfur-nitrogen dye-providing compounds will change the color characteristics of the coupler dye. Curves A and B reproduced in the FIGURE of the accompanying drawing represent, respectively, the visible absorption curves of the aldehyde substituted dye (i) illustrated below, and an analogous unsubstituted coupler dye, i.e. the dye having the formula

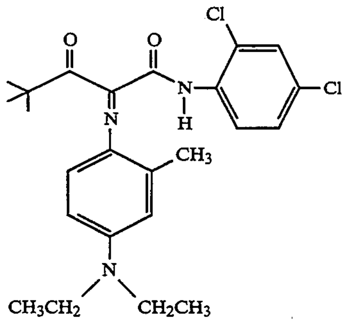

The absorption curves for both compounds were measured over the wavelength range of 350 to 800 nm in methanol solutions at the same concentrations. It will be noted that the color characteristics of the two dyes are very similar. Thus, substituting a particular coupler dye with two aldehyde moieties and alkylene linking groups in the manner taught by the present invention has substantially no influence on the color characteristics of a particular coupler dye.

While a particular dye-providing compound may be useful in one imaging system, it may need to be modified for use in another. This could be due to, among other things, differences in solubility and/or diffusibility of the dye-providing compound and/or the released coupler dye within the various imaging systems. However, one of skill in the art will be able to modify the dye-providing compounds and/or the coupler dye radical by choice of substituents, e.g. solubilizing groups, so that they will function as desired in a particular system.

Illustrative dye-providing compounds within the scope of the present invention and the coupler dyes released upon silver ion cleavage are set out in the formulae below:

| DYE-PROVIDING COMPOUND | RELEASED COUPLER DYE |
|---|---|
| (i) | |

-continued
| DYE-PROVIDING COMPOUND | RELEASED COUPLER DYE |
|---|---|
| 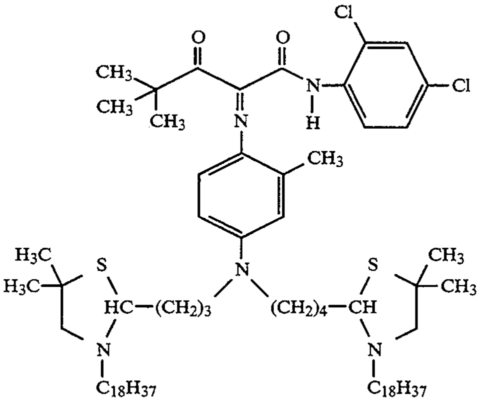 | 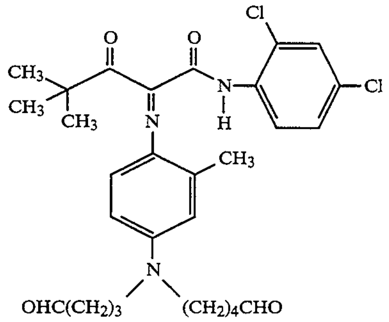 |
| (ii) 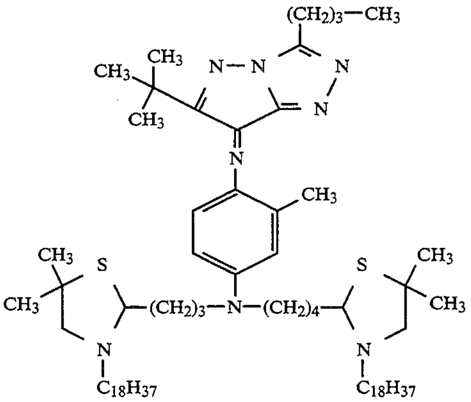 | 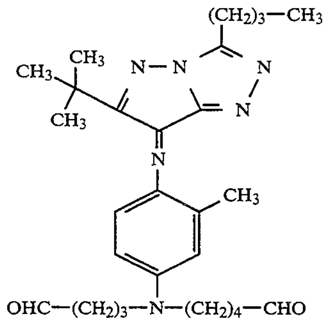 |
| (iii) 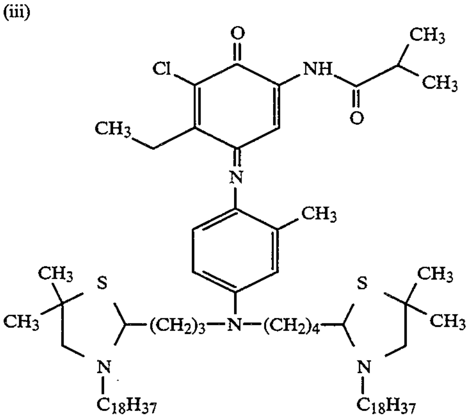 | 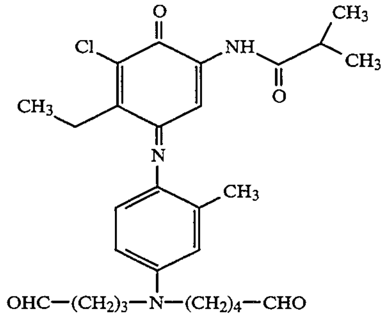 |
| (iv) 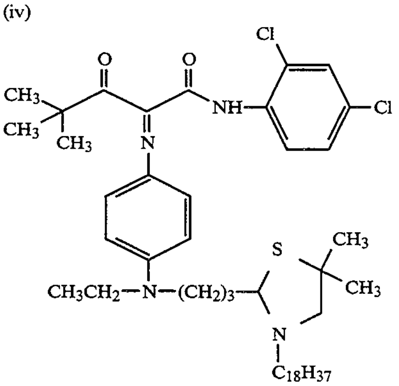 | 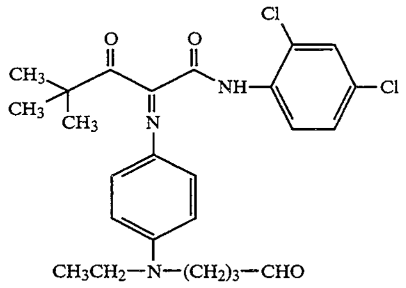 |

-continued
| DYE-PROVIDING COMPOUND | RELEASED COUPLER DYE |
|---|---|
| (v) 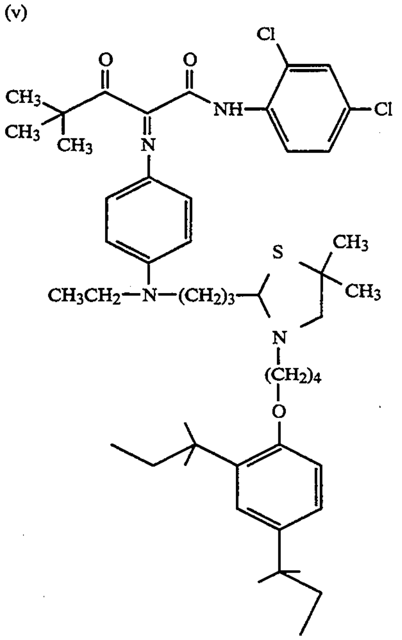 | 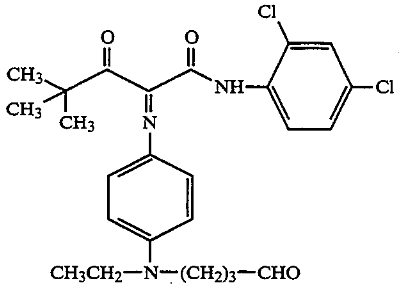 |
| (vi) 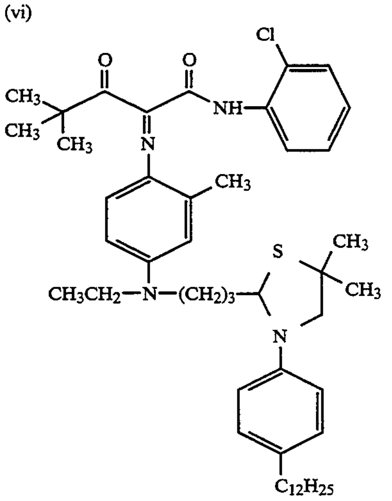 | 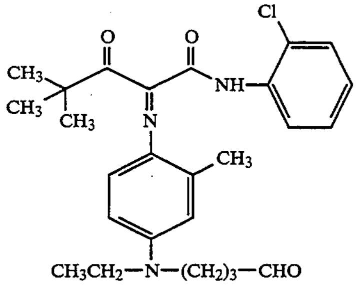 |
| (vii) 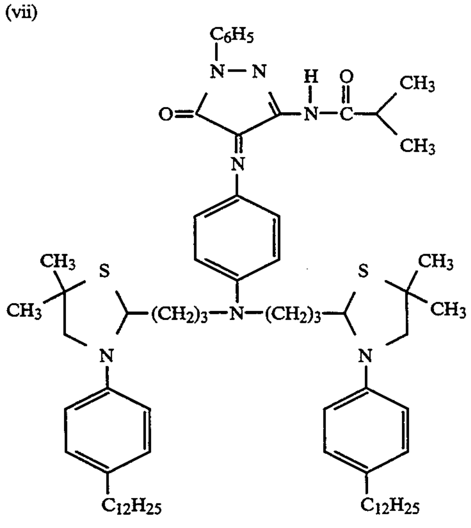 | 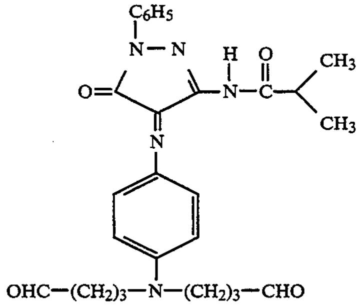 |

-continued
| DYE-PROVIDING COMPOUND | RELEASED COUPLER DYE |
|---|---|
| (viii) 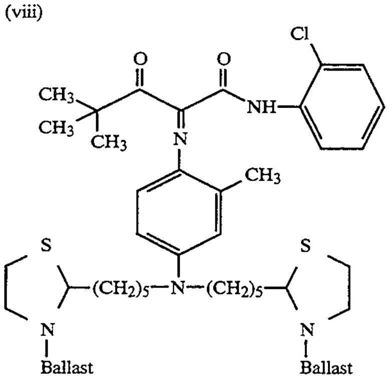 | 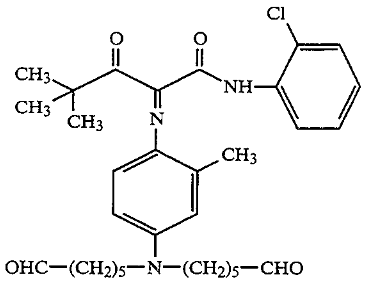 |
| (ix) 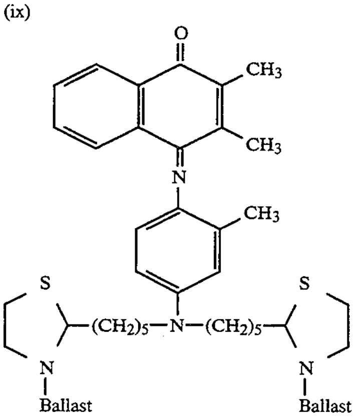 | 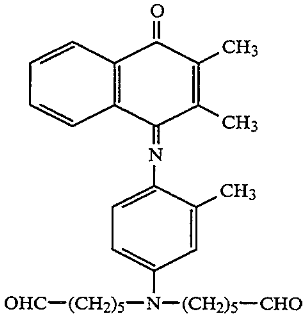 |
| (x) 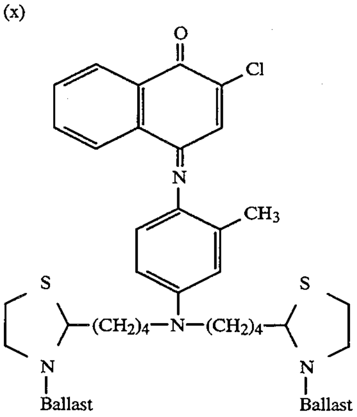 | 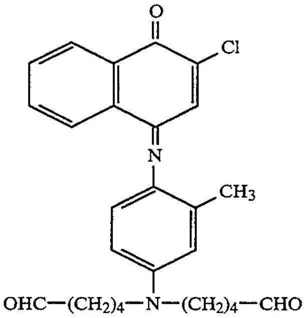 |
| (xi) 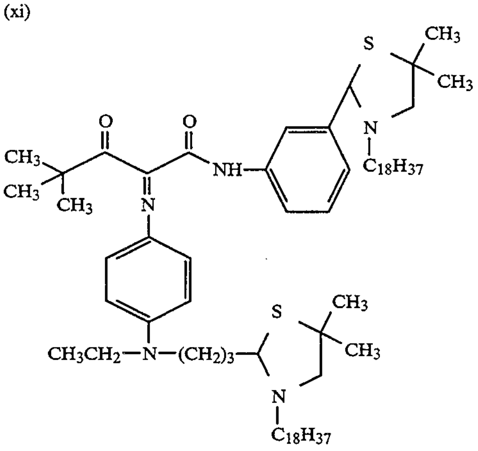 | 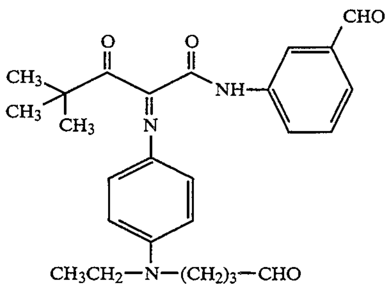 |

-continued
| DYE-PROVIDING COMPOUND | RELEASED COUPLER DYE |
| --- | --- |
| (xii) 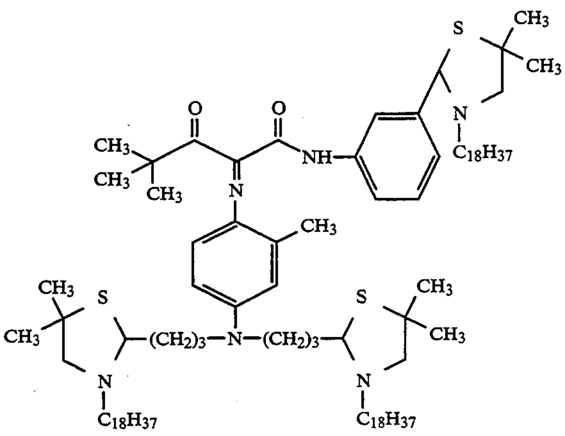 | 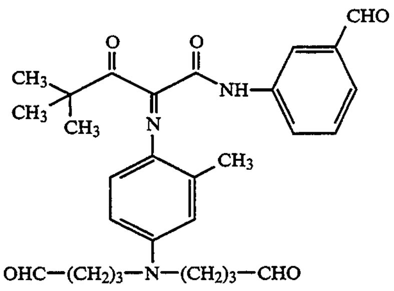 |
| (xiii) 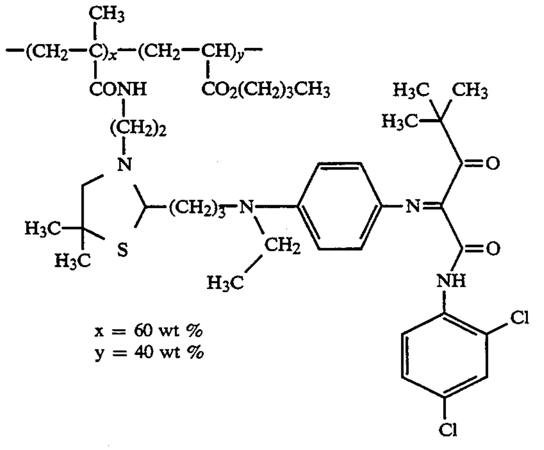 x = 60 wt % y = 40 wt % | 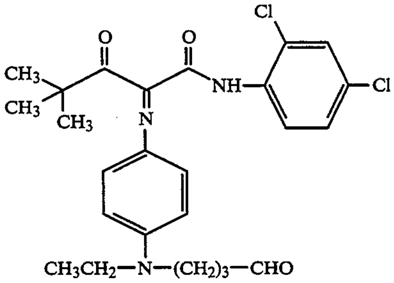 |
| (xiv) 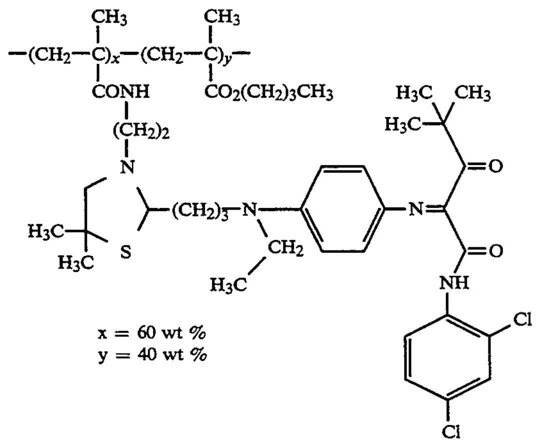 x = 60 wt % y = 40 wt % | 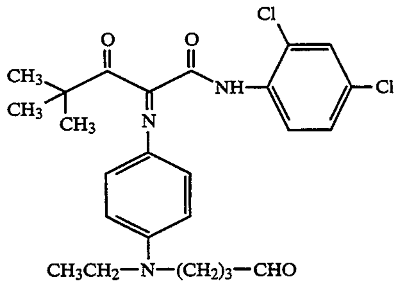 |
| (xv) | |

-continued

| DYE-PROVIDING COMPOUND | RELEASED COUPLER DYE |
| --- | --- |
| 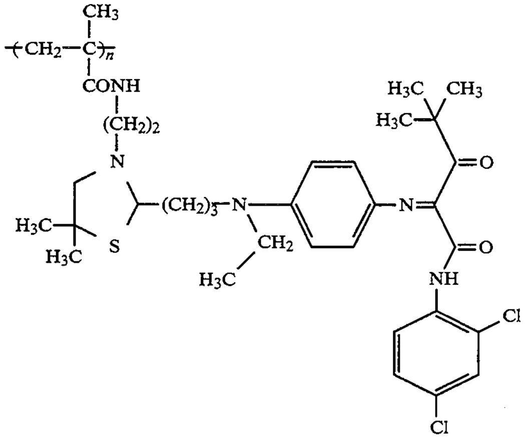 | 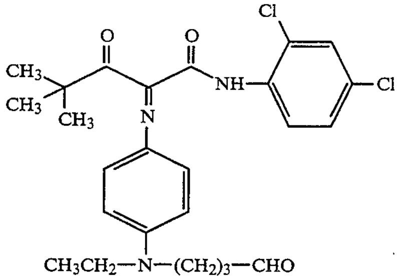 |
| (xvi) 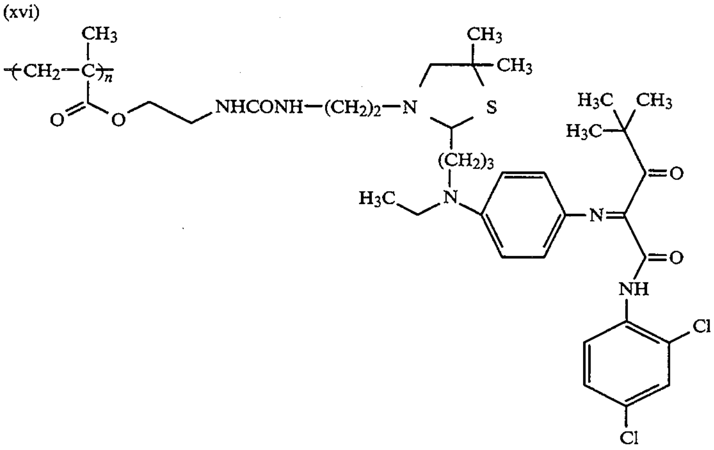 | 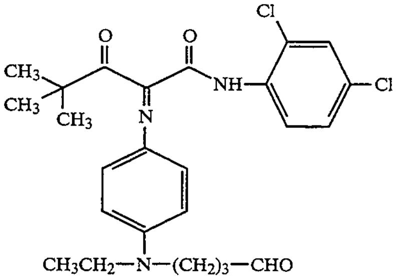 |
| (xvii) 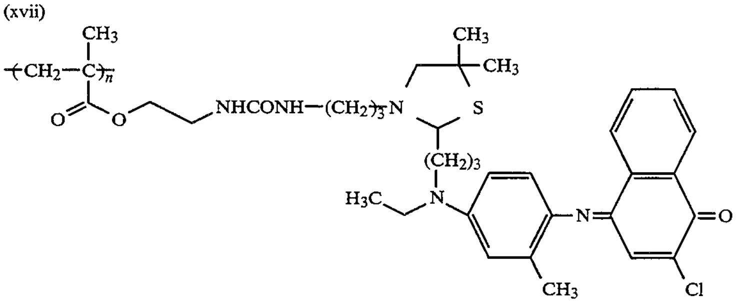 | 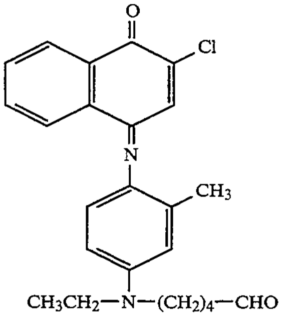 |

n in formulae (xv), (xvi) and (xvii), above, represents the number of repeating units in the polymer chain.

The dye-providing compounds of the present invention represented by (a) in Formula I which have one cyclic 1,3-sulfur-nitrogen moiety may be synthesized in the manner described in the aforementioned U.S. Pat. No. 4,098,783, by condensing an aldehyde-substituted coupler dye, e.g.

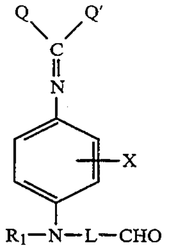

wherein Q, Q', $R_1$, X and L are as defined above, with an appropriately substituted aminoalkylthiol, i.e. HS—Z—$NHR_3$ wherein Z and $R_3$ have the same meanings given above, to yield the final dye product. Those dye-providing compounds having two cyclic 1,3-sulfur-nitrogen moieties, represented by (b) in Formula I, may be synthesized by condensing a bisaldehydic dye, e.g.,

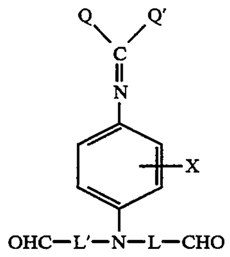

wherein Q, Q', X, L and L' are as defined above, with the appropriately substituted 2-aminoalkylthiol, e.g. 2-aminoethanethiol. It will be appreciated that a coupler dye substituted with a ketone may be substituted for the aldehyde in the above condensations. Cyclic ketones may be employed where it is desired to prepare spiro derivatives.

The mono and bisaldehyde or ketone coupler dyes used above may be prepared by an oxidative coupling reaction between, respectively, a N-hydroxyalkyl phenylenediamine and a N,N-di(hydroxyalkyl)phenylene diamine, e.g.,

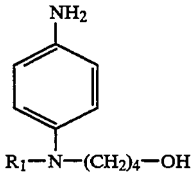

and

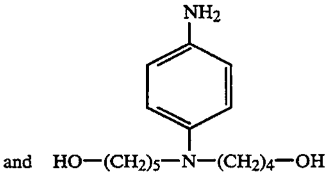

and a dye forming coupler. The oxidizing agent may be any oxidizing agent conventionally employed, e.g. potassium hexacyanoferrate(III), ammonium perchlorate, ammonium persulfate or silver oxide.

Alternatively, the N-hydroxylalkyl or N,N-di(hydroxyalkyl) phenylene diamines can be oxidized to the corresponding aldehydes or ketones and condensed with an appropriately substituted 2-aminoalkylthiol to form a thiazolidine substituted phenylene diamine. The thiazolidine substituted phenylene diamine can then be oxidatively coupled with a coupler to form the desired dye-providing compound. However, care must be taken to prevent oxidation of the cyclic 1,3-sulfur-nitrogen moiety.

The dye forming couplers may be commercially available or can be prepared by procedures well known in the art. The N-alkyl-N-hydroxyalkylphenylene diamines and the N,N-dihydroxyalkylphenylene diamines, if not commercially available, may be prepared by nucleophilic aromatic substitution reactions between p-halonitrobenzenes and hydroxyalkyl or di(hydroxyalkyl)amines followed by reduction of the aminosubstituted nitrobenzenes to the corresponding phenylenediamines. The di(hydroxyalkyl)amines can be prepared by procedures well-known in the art such as described in *Chem. Pharm. Bull.* 26 (12), 3891-3896 (1978).

The 2-aminothioalkyl compounds used above may be prepared by procedures well known in the art such as by the nucleophilic ring opening of a thioepoxide such as described in R. Luhowy et al, *J. Org. Chem.* 38 (13), 2405-2407 (1973).

Where $R_3$ represents a polymeric residue, the polymeric dye-providing compounds may also be prepared by procedures analogous to those described in the aforementioned European Patent No. 0073245 and U.S. Pat. No. 4,948,698. Preferably, the polymeric dye-providing compounds are prepared by reacting an amino substituted cyclic 1,3-sulfur-nitrogen substituted coupler dye, e.g.

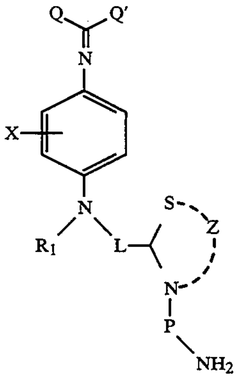

wherein Q, Q', X, $R_1$, L, P and Z are as defined above, with an acrylyl chloride, anhydride or ester, e.g. $CH_2{=}CCH_3COCl$ to form a polymerizable monomer of the formula

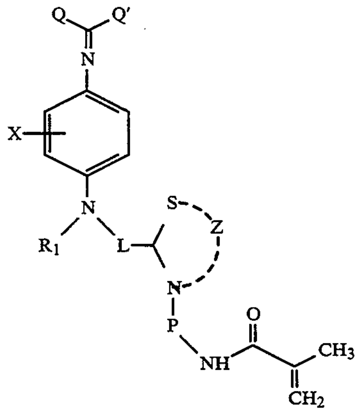

The monomer is then polymerized, according to known polymerization techniques, e.g., bulk, solution, suspension or emulsion polymerization. The polymerization may be initiated by any known method, e.g. chemically, and is generally accomplished by heating in the presence of a polymerization initiator, e.g. azobisisobutyronitrile (AIBN) or 2,2'-azobis(2-methylisopentylnitrile) (VASO 52).

Homopolymers or copolymers may be prepared. Suitable comonomers include acrylic acids, esters of acrylic acids, e.g. methyl, ethyl or butyl acrylate, or methyl, ethyl or butyl methacrylate, and styrene.

Alternatively, the polymeric dye-providing compounds of the present invention may be prepared by reacting a preformed polymer with a cyclic 1,3-sulfur-nitrogen substituted dye, e.g.

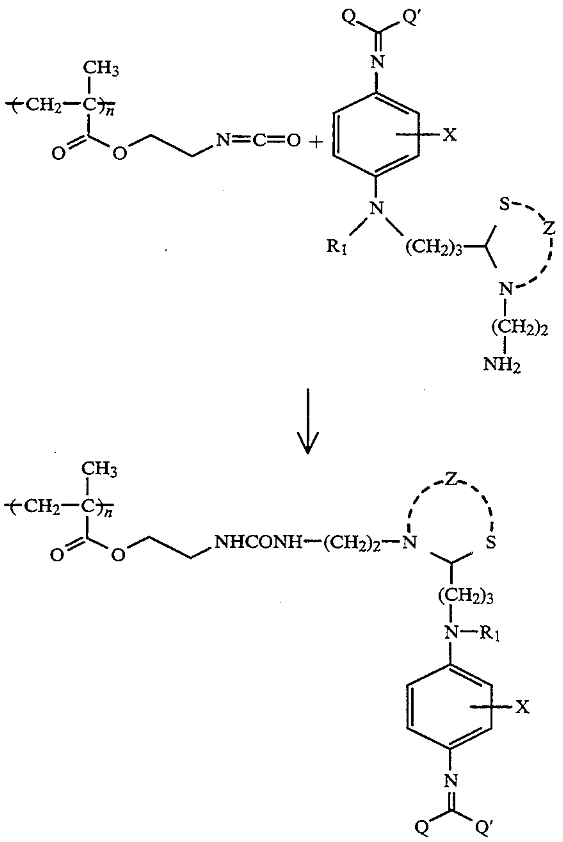

wherein Q, Q', X, $R_1$ and Z are as defined above and n represents the number of repeating units in the polymer chain.

Still other procedures for preparing the subject compounds and variations of those given above will be apparent to those skilled in the art.

The following detailed examples are given to illustrate the preparation of coupler dyes and the dye-providing compounds within the scope of this invention, and are not intended to be in any way limiting.

EXAMPLE 1

Preparation of the coupler dye and the dye-providing compound of Formula (i).

a) Preparation of 4-(N-4-hydroxybutyl)-N-(5-hydroxypentyl)amine-2-methylnitrobenzene To 185.9 mL of 5-amino-1-pentanol, chilled in an ice bath was added, dropwise, 50.5 mL of 4-chloro-1-butanol. After the addition was complete, the reaction mixture was stirred for 30 minutes, the ice bath was removed and the mixture was heated at 80° C. for 3 days. After cooling to room temperature, the mixture was washed with 100 mL of 25% NaOH. The organic portion was diluted with 200 mL of 5% methanol/-methylene chloride ($CH_2Cl_2$), dried over anhydrous magnesium sulfate, filtered and concentrated. The residue was purified by distillation, the product distilled at 80° C. (0.05 mm) to yield 38.51 g of N,N-4-hydroxybutyl-5-hydroxypentylamine. The structure was confirmed by NMR and Mass Spectroscopy.

To 27.6 g of 4-hydroxybutyl-5-hydroxypentylamine was added 21.2 mL of 5-fluoro-2-nitrotoluene. The resulting mixture was heated at 65° C. for 24 hours. The product was purified by HPLC to yield 27 g of 4-(N-4-hydroxybutyl-N-(3-methyl-4-nitrophenyl)amino)-1-pentanol. The structure was confirmed by NMR and Mass Spectroscopy.

b) Preparation of the dihydroxy coupler dye

To 7.5 g 4-(N-4-hydroxybutyl-N-(3-methyl-4-nitrophenyl)amino)-1-pentanol was added 30 mL absolute ethanol and 2 g zinc dust. The resulting yellow mixture was refluxed for approximately 1 hour, during which time 8 mL of concentrated hydrochloric acid was added until a clear mixture resulted. The reaction mixture was cooled and filtered. With rapid stirring, the filtrate was added to a mixture containing 33.4 g potassium carbonate, 100 mL water and 6.95 g of N-(2,4-dichloro-phenyl)-4,4-dimethyl-3-oxopentamide (which was prepared by the procedure described in U.S. Pat. No. 3,408,194). After stirring for 15 minutes, a solution of 31.8 g of potassium hexacyanoferrate(III) in 150 mL water was added dropwise. After the addition was completed, the reaction was stirred at room temperature for one hour. The organic layer was separated, dried and concentrated. The residue was purified by HPLC to yield 5.7 g of the dihydroxy coupler dye. NMR and Mass Spectroscopy confirmed the structure.

c) Preparation of the title dialdehyde coupler dye 1.86 mL oxalyl chloride was dissolved in 46 mL of dry ($CH_2Cl_2$) The solution was placed under nitrogen and chilled to −70° C. To the chilled solution was slowly added a solution of 3.1 mL dimethylsulfoxide in 9 mL dry $CH_2Cl_2$. After stirring for 5 minutes at −70° C., a solution containing 5.6 g of the dihydroxy coupler dye, prepared in step a, in 50 mL of dry $CH_2Cl_2$ was added and the mixture was allowed to stir for 15 minutes while maintaining the temperature below −50° C. The reaction mixture was quenched using 13.8 mL of triethylamine and then allowed to come to room temperature. 100 mL water was added and the organic layer was separated, dried and concentrated. The residue was purified by HPLC to yield 2.8 g of the dialdehyde coupler dye. NMR and mass spectroscopy confirmed the structure.

d) Preparation of the title dye-providing compound

To 0.92 g sodium bicarbonate and 4.3 g of 1-(N-octadecylamino)-2-methyl-2-propanethiol hydrochloride dissolved in 30 mL of absolute ethanol was added a solution of 2.8 g of the dialdehyde coupler dye, prepared in step c, in 30 mL of absolute ethanol. The resulting mixture was refluxed for 12 hours and condensed under reduced pressure. The resulting residue was purified by HPLC to yield 4.3 g of the title dye-providing compound. NMR and Mass Spectroscopy confirmed the structure.

In addition to the above, the specific dye-providing compounds of Formulae (ii) and (iii) were also prepared in accordance with the foregoing procedure by substituting the appropriate dye-forming coupler in place of N-(2,4-dichlorophenyl)-4,4-dimethyl-3-oxopentanamide.

The dye-providing compound of Formula (iv) was prepared in the same manner as Example 1 except that 4-(N-ethyl-N-4-hydroxybutylamino)aniline.$H_2SO_4$ (Witton Chem. Co., England) was used in place of 4-(N-4-hydroxybutyl-N-(3-methyl-4-nitrophenyl)amino)-1-pentanol. The dye-providing compound of Formula (v)

was also made in an analogous manner to that of (iv) above, using the appropriately substituted 2-aminoethanethiol.

The dye-providing compound of Formula (xi) was prepared according to the procedure used in Example 1 using the dialdehyde coupler dye of Formula (xi) and the appropriately substituted 2-aminoethanethiol. The coupler dye of Formula (xi) was prepared as follows:

200 g of 3-aminobenzylalcohol were dissolved in 2000 mL of xylene at 90°-100° C. under nitrogen with stirring. To the resulting stirred solution was added, dropwise over a one-hour period, 231 g of methyl 4,4'-dimethyl-3-oxovalerate. The resulting mixture was refluxed for one hour. The mixture was then distilled to remove the methanol generated upon formation of the amide. The resulting solution was cooled causing a precipitate to be formed. The precipitate was filtered, washed with hexane, and was dissolved in chloroform. The chloroform solution was extracted two times with a 1% hydrochloric acid solution, dried over sodium sulfate, and filtered. The resulting solution was concentrated to approximately 2500 mL, heated to redissolve the solid and was then cooled. The resulting precipitate was filtered and recrystallized from hexane to yield 131 g of N-(2-hydroxymethylphenyl)-4,4-dimethyl-3-oxopentamide. The structure was confirmed by $^1$HNMR spectroscopy.

The N-(2-hydroxymethylphenyl)-4,4-dimethyl-3-oxopentamide was oxidatively coupled with 4-(N-ethyl-N-4-hydroxybutylamino) aniline.$H_2SO_4$ as in step (b) of Example 1 and then oxidized as in step (c) of Example 1 to yield the title coupler dye. The structure was confirmed by $^1$HNMR.

As demonstrated in preparing the dye-providing compounds of Formulae (i)-(iii) above, one can easily synthesize the color coupler dyes containing the necessary aldehyde moieties for use in the present invention by readily modifying a known phenylene diamine developer, coupling it with any dye-forming coupler moiety and oxidizing the resulting alcohol(s) substituted coupler dyes. The resulting aldehyde and/or ketone coupler dyes can then be used to make the dye-providing compounds as described above. This obviates the need to modify each coupler with an aldehyde and/or ketone moiety and having to worry about the influence it will have on the chromophore of the resulting coupler dye. Thus, the particular substitution of the phenylene diamine according to the present invention allows for the use of one phenylene diamine color developer to readily and easily synthesize a variety of coupler dyes, knowing in advance the color characteristics of the resulting coupler dye.

Preparation of the polymeric dye-providing compounds of the present invention.

Weight average molecular weight values, (Mw), for the polymeric color-providing materials were determined by gel permeation chromatography, GPC, using a refractive index detector. The unit was calibrated with a series of narrow molecular weight distribution polystyrene standards covering the molecular weight range of 580 to >1 million Daltons. The polymer solvent and GPC mobile phase was tetrahydrofuran which contained 2.5 mM triethylamine added to eliminate solute interactions with the column packing. Molecular weight values obtained for the polymeric color-providing materials were based on the polystyrene narrow standards calibration and are therefore not absolute. They are reported in terms of the polystyrene molecular weight(s) with equivalent hydrodynamic volume(s).

EXAMPLE 2

A polymeric dye-providing compound corresponding to formula (xiii) was prepared as follows: A solution of 1.24 g of the aminoethylthiazolidine dye having the structure

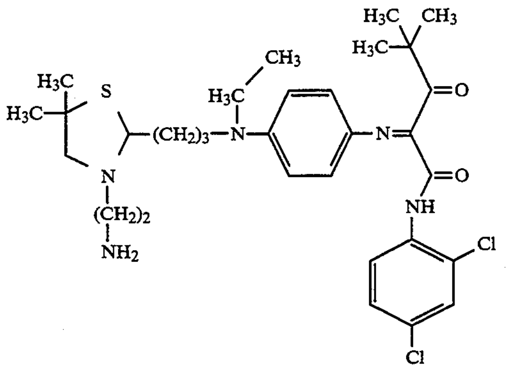

and 0.28 g of triethylamine in 30 mL of dry tetrahydrofuran (THF) was cooled to 0° C. To the cooled solution, was added dropwise over 15 minutes, a solution of methacryloyl chloride in 10 mL dry THF. After the mixture had stirred at 0° C. for 15 minutes, it was filtered and the filtrate was evaporated in vacuo to yield 1.38 g of residue. The residue was purified by column chromatography (silica gel) using $CH_2Cl_2$ and 1% and 1.5% methanol in $CH_2Cl_2$. $^1$HNMR and mass spectroscopy confirmed the structure of the monomer, i.e.

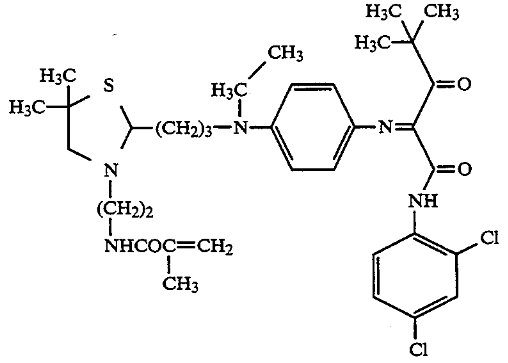

To a solution of 3.10 g of the monomer and 2.055 g of n-butylacrylate in 6.2 mL of dry dimethylformamide (deairated by bubbling in nitrogen for ½ hour) at 70° C. under nitrogen was added 100 mg of 2,2'-azobis(2-methylisopentylnitrile) (VASO 52). The resulting mixture was stirred at 70° C. under nitrogen for 3 hours, and then an additional 100 mg VASO 52 was added. Heating at 70° C. under nitrogen was continued for an additional 16 hours, after which time the reaction was allowed to cool to room temperature. The reaction was quenched with water and then extracted two times with $CH_2Cl_2$. The combined $CH_2Cl_2$ extracts were washed with water, dried over anhydrous sodium sulfate, filtered and concentrated in vacuo to yield a gummy material. The gummy material was chromatographed on silica gel using $CH_2Cl_2$, 1% methanol in $CH_2Cl_2$ and 2% methanol in $CH_2Cl_2$ to remove unreacted monomer and other impurities. 10% methanol in $CH_2Cl_2$ was used to elute the title polymeric dye (xiii). IR and NMR were used to confirm the structure. The weight average molecular weight (Mw) was determined to be 10,188.

EXAMPLE 3

Three polymeric dye-providing compounds corresponding to formula (xiv) were prepared by procedures analogous to that used to prepare the compound of formula (xiii) except that n-butylmethacrylate replaced the n-butylacrylate. For the preparation of the first two polymeric dyes corresponding to formula (xiv), i.e. (xiv(a)) and (xiv(b)), the same ratio of reactants was employed. For the third polymeric dye conforming to formula (xiv), i.e. (xiv(c)), the molar ratio of n-butylmethacrylate to dye monomer was 6/1 instead of 3.56/1. The Mw for the 3 polymers thus prepared were:

| | |
|---|---|
| (xiv(a)) | 25,815 |
| (xiv(b)) | 26,841 |
| (xiv(c)) | 36,815 |

EXAMPLE 4

The polymeric dye-providing material of formula (xv) was prepared and purified by a procedure analogous to that used to prepare the compound of formula (xiii) except that there was no comonomer, i.e. n-butylacrylate, present. Mw=6,092.

EXAMPLE 5

The polymeric dye-providing material of formula (xvi) was prepared as follows:

To 6.8 mL of a solution of poly(isocyanatoethyl methacrylate), prepared according to the procedure described in U.S. Pat. No. 4,952,640 issued Aug. 28, 1990, using the same quantity of starting materials, was added an additional 50 mL of dry toluene. To this solution, under nitrogen, was added 1 g of the aminoethylthiazolidine dye used to make the dye monomer for preparing the compound of formula (xiii), above, in 40 mL of dry dimethyl formamide. The resulting mixture was stirred and heated at 50°-55° C. under nitrogen, for 20 hours. The reaction mixture was then allowed to cool to room temperature and the toluene and most of the dimethylformamide were removed in vacuo. The residual solution was then added dropwise, with stirring, to 40 mL methanol. The methanol was decanted from the gummy precipitate which had formed. The precipitate was rinsed several times with dry methanol from which the resulting semi-solid was filtered and dried in vacuo at 45° C. to yield 171 mg of the title polymeric dye-providing material, Mw=12,509.

The aminoethylthiazelidine dye used in the preparation of the compound of formula (xiii) was prepared by a procedure analogous to that used in step (d) of Example 1 using the aldehyde coupler dye of formula (iv) in place of the dialdehyde coupler dye and 1,1-dimethyl-2-(2-amino)ethylaminoethanethiol in place of (N-octadecylamino)-2-methyl-2-propanethiol hydrochloride. The 1,1-dimethyl-2-(2-amino)ethylaminoethanethiol was prepared as follows:

To a solution of 30.64 g of N-acetylethylenediamine in 550 mL dry benzene were added 30.95 g of bis-(isobutyraldehyde)disulfide, and the mixture was stirred and azeotroped, under nitrogen for 3.25 hours. The benzene solution was condensed in vacuo to anvil. The oil was triturated with petroleum ether (pet. ether) twice, each time the pet. ether was decanted from the oil. The oil was dried in vacuo at room temperature to yield the desired Schiff's base.

To a solution of 56.2 g of the Schiff's base in 600 mL ethanol was added, with stirring under nitrogen, 22.71 g of sodium borohydride. The mixture was allowed to stir at room temperature for 18 hours. The reaction was then quenched with an ice cold hydrochloric acid solution (pH~1). The resulting aqueous mixture was extracted twice with methylene chloride ($CH_2Cl_2$). The aqueous mixture was made strongly alkaline with a sodium hydroxide solution and again extracted twice with $CH_2Cl_2$. The combined $CH_2Cl_2$ extracts were dried over anhydrous sodium sulfate, and evaporated in vacuo to yield an oil. The oil was dried in vacuo to yield 47.3 g of the desired diacetamide.

To a stirred solution of 55.8 g of the diacetamide in 250 mL ethanol, under nitrogen, was added 250 mL of 6N sodium hydroxide. The resulting mixture was then stirred and refluxed for 20.5 hours. After cooling to room temperature, the reaction mixture was diluted with 300 mL water. The aqueous mixture was extracted three times with $CH_2Cl_2$. The $CH_2Cl_2$ extracts were combined and dried over anhydrous sodium sulfate. The $CH_2Cl_2$ was concentrated in vacuo to yield an oil. The oil was dried at room temperature in vacuo to yield 36.5 g of the desired adisulfide.

To a solution of 36 g of the adisulfide in 740 mL ethanol was added, with stirring and cooling (ice bath), 204 mL concentrated hydrochloric acid. To this mixture was added, portionwise over 1.5 hours under nitrogen, 37.0 g of zinc dust. A thick paste was formed. After allowing the reaction to stand for 1 hour, 125 mL ethanol was introduced and stirring was commenced. After 18 hours, the mixture was filtered, and the precipitate was washed with a 4:1 mixture of ethanol:concentrated hydrochloric acid. The combined filtrates were concentrated in vacuo to a small volume. To this was added isopropanol. The precipitates which had formed were filtered, washed with isopropanol and dried in vacuo, over sodium hydroxide, to yield 30 g of 1,1-dimethyl-2-(2-amino)ethylaminoethanethiol.

The bis(isobutyraldehyde) disulfide used above was prepared as follows:

To a solution of 57.8 g of isobutyraldehyde in 100 mL of chloroform at 25° C. was added dropwise 54 g of freshly distilled sulfur monochloride. The rate of addition was adjusted so as to maintain the temperature below 40° C. After the addition was complete, the chloroform was removed in vacuo and the residue was distilled to yield bis(isobutyraldehyde) disulfide, 81°- 84° C. (0.4 mm). The structure was confirmed by spectral analysis.

As noted earlier, the dye-providing compounds according to the present invention are useful for forming color images in thermographic imaging systems processed by imagewise heating and in photographic imaging systems utilizing silver halide wherein the method of processing employs either wet processing to develop the image or thermal processing which develops the image by heating. Of particular interest are the heat-developable imaging systems.

Specifically, the present invention provides an image-recording material for use in a diffusion transfer color process comprising (a) one or more supports, each carrying in one or more layers a source of silver ions and a dye-providing compound capable of releasing a diffusible coupler dye upon cleavage in the presence of silver ions, said dye-providing compound represented by formulae I(a) or (b) defined above, and (b) on the same or a separate support, an image receiving layer capable of receiving the diffusible coupler dye released from said dye-providing compound.

For photographic and photothermographic applications, the color photosensitive image-recording material includes a photosensitive silver halide which could also function as the silver ion source. Preferably, in photothermographic systems the photosensitive image-recording material additionally contains a silver salt oxidizing material and a reducing agent for silver.

In another embodiment, the photothermographic and the thermographic color imaging-recording materials may also include an auxiliary ligand for silver. The use of auxiliary ligands in thermographic and photothermographic image-recording materials forms the subject matter of the copending U.S. patent application of J. Freedman, S. Sofen and K. Young, Ser. No. 07/923,858 filed Jul. 31, 1992, now abandoned in favor of C.I.P. application Ser. No. 079,146, now U.S. Pat. No. 5,328,799.

As mentioned earlier, the dye-providing compounds of the present invention are substantially non-diffusible in the thermographic, photographic and photothermographic materials but are capable of undergoing cleavage in the presence of the imagewise distribution of silver ions and/or soluble silver salt complex made available in the undeveloped and partially developed areas as a function of development to liberate a more mobile and diffusible coupler dye in a corresponding imagewise distribution.

For forming color images in photographic image-recording systems, a dye-providing compound according to the present invention can be used in both monochrome and full-color imaging systems such as disclosed in the aforementioned U.S. Pat. No. 4,098,783 issued Jul. 4, 1978, and U.S. Pat. No. 3,719,489 issued Mar. 6, 1973, both of Ronald F. W. Cieciuch et al. Generally, a dye-providing compound is associated with a light-sensitive silver halide emulsion which, after being exposed, is developed with an aqueous alkaline processing solution including a silver halide developing agent and a silver halide solvent. The imagewise distribution of silver ions such as contained in the soluble silver complex made available during processing of the emulsion migrates to the associated color-providing material which undergoes cleavage in the presence of the complex to release an imagewise distribution of the more diffusible coupler dye. The subsequent formation of a color image is the result of the differential in diffusibility between the dye-providing compound and the liberated coupler dye whereby the imagewise distribution of the more diffusible coupler dye released in undeveloped and partially developed areas is free to transfer to the image-receiving layer. The color photographic image-recording materials using the compounds of this invention can be prepared in accordance with such procedures as described in the aforementioned U.S. Pat. No. 4,098,783 of Ronald F. W. Cieciuch et al issued Jul. 4, 1978 and the U.S. Pat. No. 3,719,489 of Ronald F. W. Cieciuch et al issued Mar. 6, 1973, the disclosures of both being herein incorporated by reference.

In addition to the full color photographic systems described above, the dye-providing compounds of the present invention may be used as the image dye-releasing thiazolidines in subtractive color transfer films which utilize two different imaging mechanisms: dye developers and image dye-releasing thiazolidines described in U.S. Pat. No. 4,740,448 issued Apr. 26, 1988 to Peter O. Kliem.

The color photothermographic image-recording materials using the compounds of this invention can be prepared in accordance with such procedures as disclosed in Research Disclosure No. 17029, issued June 1978. The thermographic image recording materials using the compounds of this invention can be prepared as described in the aforementioned copending U.S. patent application, Ser. No. 07/923,858 of J. R. Freedman et al and the copending U.S. patent application, Ser. No. 07/994,898 of J. R. Freedman et al filed Dec. 22, 1992.

The source of silver ions may be any of those materials commonly employed in the photographic art to provide silver ions provided the silver ion is made available imagewise upon processing to cleave the cyclic 1,3-sulfur-nitrogen moiety(ies) of the dye-providing compound and release the diffusible coupler dye. Useful materials include silver halides and any of the silver salt oxidizing materials known in the art, such as those described in the aforementioned Research Disclosure No. 17029, issued June 1978. For thermographic applications, the silver salt complexes disclosed in the aforementioned copending U.S. patent application, Ser. No. 07/994,898 of J. R. Freedman et al filed Dec. 22, 1992, are particularly useful.

The photosensitive silver halide used in the present invention may be any photosensitive silver halide employed in the photographic art, such as, silver chloride, iodide, bromide, iodobromide, chlorobromide, etc. and it may be prepared in situ or ex situ by any known method including adding a source of halide ions to the silver salt oxidizing material in a suitable vehicle such as described in the aforementioned Research Disclosure No. 17029.

The photosensitive silver halide emulsions used in the present invention may be spectrally sensitized by any known method in order to extend the photographic sensitivity to wavelengths other than those absorbed by the silver halide. Examples of suitable sensitizers include cyanine dyes, merocyanine, styryl dyes, hemicyanine dyes and oxonole dyes.

In addition to spectral sensitization, the silver halide emulsion may be chemically sensitized using any method known in the photographic art.

The silver halide emulsion is generally added to each photosensitive layer in an amount calculated to give a coated coverage in the range of 0.5 to 8.0 $mmol/m^2$, preferably 0.5 to 4.0 $mmol/m^2$.

As mentioned above, the source of silver ions may be any of the silver salt oxidizing materials known in the art provided they are relatively light stable and thermally stable under the processing conditions and provided further that they become available to cleave the dye-providing material during processing. The silver salt oxidizing material is generally an organic silver salt or silver salt complex as heretofore known in the art. Any organic compound known in the photographic art to be useful for forming the organic silver salt may be employed, see, e.g., those described in U.S. Pat. No. 4,729,942. See U.S. Pat. No. 4,260,677 for useful silver salt complexes.

Examples of suitable silver salt oxidizing materials include silver salts of carboxylic acids, e.g., behenic and stearic acids and silver salts of compounds having an imino group. Preferred silver salts are the organic silver salts having an imino group. The silver salt of benzotriazole has been found to give good results in the heat-developable photosensitive systems of the present invention particularly when used with the auxiliary ligands described in more detail hereinafter.

The silver salt oxidizer used in the present invention can be prepared in a suitable binder by any known means and then used immediately without being isolated. Alternatively, the silver salt oxidizer may be isolated and then dispersed in a suitable binder.

The silver salt oxidizer is generally used in an amount ranging from 0.5 to 8.0 mmol/$m^2$, and preferably from 0.5 to 4.0 mmol/$m^2$.

The reducing agents which may be used in the present invention may be selected from among those commonly used in heat-developable photographic materials. Illustrative reducing agents useful in the present invention include hydroquinone and its derivatives, e.g., 2-chlorohydroquinone; aminophenol derivatives, e.g., 4-aminophenol and 3,5-dibromophenol; catechol and its derivatives, e.g., 3-methoxycatechol; phenylenediamine derivatives, e.g., N,N-diethyl-p-phenylenediamine; and, 3-pyrazolidone derivatives, e.g., 1-phenyl-3-pyrazolidone and 4-hydroxymethyl-4-methyl-1-phenyl-3-pyrazolidone. The preferred reducing agents are 1-phenyl-3-pyrazolidone, commercially available under the tradename Phenidone, 4,4-dimethyl-1-phenyl-3-pyrazolidone, commercially available under the tradename Dimezone, and 4-hydroxymethyl-4-methyl-1-phenyl-3-pyrazolidone, commercially available under the tradename Dimezone-S.

The reducing agents may be used singly or in combination and they are generally employed in amounts ranging from 0.5 to 8.0 mmol/$m^2$, and preferably 1.0 to 4.0 mmol/$m^2$.

Thermal solvents are compounds which are solids at ambient temperature but which melt at the temperature used for processing. The thermal solvent acts as a solvent for various components of the heat-developable materials, it helps to accelerate thermal development and it provides the medium for diffusion of various materials including silver ions and/or complexes, reducing agents and the dyes. Illustrative thermal solvents useful in the present invention include polar organic compounds such as the polyglycols described in U.S. Pat. No. 3,347,675 and the compounds described in U.S. Pat. No. 3,667,959. Particularly useful compounds include urea derivatives, e.g., dimethylurea, diethylurea and phenylurea; amide derivatives, e.g., acetamide, benzamide and p-toluamide; sulfonamide derivatives, e.g., benzenesulfonamide and $\alpha$-toluenesulfonamide; and polyhydric alcohols, e.g., 1,2-cyclohexanediol and pentaerythritol. The thermal solvent designated TS-1 and having the structure

TS-1

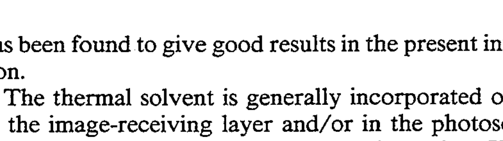

has been found to give good results in the present invention.

The thermal solvent is generally incorporated on or in the image-receiving layer and/or in the photosensitive silver halide layer of the present invention. However, it may also be added to any intermediate layers and protective layers where necessary to obtain a desired result.

The thermal solvent is generally added in each layer in amounts ranging from 0.5 to 10.0 g/$m^2$, preferably 1.0 to 5.0 g/$m^2$.

The photosensitive silver halide emulsion layer(s) and other layers of the heat-developable photosensitive image-recording material may contain various materials as binders. Suitable binders include water soluble synthetic high-molecular weight compounds such as polyvinyl alcohol and polyvinylpyrrolidone and, synthetic or natural high-molecular weight compounds such as gelatin, gelatin derivatives, cellulose derivatives, proteins, starches and gum arabic. A single binder or mixture of binders may be used. Gelatin is the preferred binder for use in each layer.

The amount of binder used in each layer is generally 0.5 to 5.0 g/$m^2$, preferably 0.5 to 3.0 g/$m^2$.

The layers of the heat-developable photosensitive system according to the present invention which contain a crosslinkable colloid as a binder, e.g., gelatin, can be hardened by using various organic and inorganic hardeners such as those described in T. H. James, *The Theory of the Photographic Process,* 4th Ed., MacMillan, 1977, pp. 77–87. The hardeners can be used alone or in combination. It is preferred that the image-recording material according to the present invention contains a hardener in the photosensitive silver halide emulsion layer. Any suitable hardener known in the photographic art may be used, however, aldehyde hardeners, e.g. succinaldehyde and glyoxal, have been found to be particularly useful when gelatin is employed as the binder.

The hardeners are generally used in amounts ranging from 1 to 10% by weight of the total amount of gelatin coated.

The dye-providing compound may be present in the same layer as the silver ion source including the photosensitive silver halide emulsion layer or in a layer on either side of the layer containing the silver ion source or the photosensitive emulsion layer. However, in photosensitive systems wherein the dye-providing compound is also a dye, it is generally preferred that the dye-providing compound be placed so that exposure does not occur through it. If exposure is made through the dye-providing compound, the dye-providing compound may absorb the light needed to expose the silver halide. However, if the cyclic 1,3-sulfur-nitrogen substituted coupler dyes described in Formula I(a) and (b) above are used in their colorless leuco form, exposure could occur through the dye-providing compound. The leuco form of coupler dyes are well known in the art and are discussed, e.g., in the aforementioned James, T. H., *The Theory of the Photographic Process,* Fourth Ed., MacMillan Publishing Co., Inc., New York, 1977, pp. 341–343. Conversion of the leuco dye to the color coupler dye would occur some time after exposure, before or after cleavage of the cyclic 1,3-sulfur-nitrogen moiety including after transfer to the receiving layer.

In certain instances, it may be desirable to separate the dye-providing compound from the emulsion layer by a spacer layer. Where the particular dye-providing compound chosen tends to be migratory during storage and/or thermal development of the heat-developable system, it is preferred that the dye-providing compound be in a separate layer and more preferably, that it be in a layer furthest from the image-receiving layer.

The amount of dye-providing compound used varies with the type chosen but generally an amount of 0.25 to 2.0 mmol/$m^2$ is used.

The dye-providing compounds may be incorporated into the thermosensitive layer(s) of the heat-developable photosensitive and thermographic systems by any suitable method. For example, the dye-providing compounds can be dissolved in a low boiling and/or high boiling solvent and dispersed in the binder, they can be dispersed in aqueous solutions of suitable polymers, e.g., gelatin, by means of a ball mill, or they can be solvent coated using any organic solvent that will also dissolve the binder, e.g., trifluoroethanol or dimethylsulfoxide (DMSO) can be used as solvents for gelatin.

Auxiliary ligands for silver which can be used in the present invention include 2,2'-bipyrimidine; 1,2,4-triazole and derivatives thereof, e.g., 3-phenyl-5-thienyl-1,2,4-triazole; phosphines, e.g., triphenylphosphine; acyclic thioureas, e.g., N,N'-di-n-butylthiourea and tetramethylthiourea; 3,6-dithia-1,8-octanediol; 6-substituted purines wherein the 6-position is substituted with —OR or —NHR' where R is hydrogen, alkyl, or aryl and R' is alkyl, e.g., 6-methoxypurine and 6-dodecylaminopurine; and, bidentate nitrogenous ligands having two nitrogen atoms which are both available to coordinate to the same silver atom, e.g., 4-azabenzimidazole and derivatives thereof, 2,2'-dipyridyls including 2,2'-dipyridyl, 4,4'-dimethyl-2,2'-dipyridyl and 4,4'-diphenyl-2,2'-dipyridyl and 1,10-phenanthrolines including 1,10-phenanthroline, 5-chloro-1,10-phenanthroline and 5-nitro-1,10-phenanthroline.

When employed, the auxiliary ligand may be present in any layer of the heat-developable photosensitive or thermosensitive system of the present invention including the image-receiving layer. If present in a layer on the image-receiving layer, the layer also preferably contains a thermal solvent in which the ligand is soluble and a binder. Alternatively, water Soluble ligands may be coated on the negative, i.e. on the layer comprising the photosensitive silver halide, before or after hardening of the gel has been accomplished. If the silver assisted cleavage of the particular dye-providing compound tends to be slow, it is preferred that the auxiliary ligand be present in a layer other than the image-receiving layer.

The auxiliary ligands are generally used in amounts which yield, after drying, a coating coverage of 1 to 36 mmol/$m^2$, preferably 2 to 24 mmol/$m^2$.

Silver salt complexes which are suitable for use in the thermographic systems of the present invention include those silver salt complexes formed by the combination of a) one monovalent silver ion;
b) at least one coordinating ligand, the ligand(s) having all its available ligating sites coordinated to said one monovalent silver ion, said ligand(s) being sufficient to fully coordinate said silver ion, i.e., the silver ion is incapable if accepting lone pairs of electrons from any other potential donating atom or ligand; and,
c) a monovalent anion having a silver binding constant of less than 1, said silver salt complex having a gross stability constant between 2.5 and 12 as described in the aforementioned copending U.S. patent application of J. R. Freedman et al, Ser. No. 07/994,898. Specific examples of the silver salt complexes falling within the above definition include silver$(2,2'\text{-bipyridyl})_2$ toluate, silver(4,4'-dimethyl-2,2'-bipyridyl) octanesulfonate, silver(4,4'-diphenyl-2,2'-bipyridyl) tosylate, silver$(2,2'\text{-biquinoyl})_2$ tosylate, silver$(1,10\text{-phenanthroline})_2$ nitrate, silver$(5\text{-chloro-}1,10\text{-phenanthroline})_2$ tosylate, and silver$(5\text{-nitro-}1,10\text{-phenanthroline})_2$ tosylate.

The support for the image-recording elements according to the present invention must necessarily be able to withstand the heat required for processing the image, and any suitable support can be employed such as those described in Research Disclosure No. 17029, issued June 1978. Specific examples of suitable supports include synthetic plastic films, such as a polyester film, a polyvinyl chloride film or a polyimide film and paper supports, such as, photographic raw paper, printing paper, baryta paper and resin-coated paper. Preferably, a polyester film is used.

A subcoat may be added to the face of the support which carries the heat-developable materials in order to increase adhesion. For example, a polyester base coated with a gelatin subcoat has been found to enhance adhesion of aqueous based layers.

The heat-developable image-recording materials according to the present invention can be used to form monochrome or multicolor images. If the photosensitive image-recording material is to be used to generate a full color-image, it generally has three different heat-developable light-sensitive layers each releasing a different color dye as a result of thermal development. For the thermographic image-recording materials, full color images may be obtained by using the three subtractive primaries: yellow, magenta and cyan. This may be achieved by employing three separate thermosensitive sheets, each designed to release a different diffusible dye. The image to be reproduced is generally separated into its blue, green and red components and each color record is printed in registration, using the corresponding thermosensitive sheet, on the same receiving sheet in a manner analogous to that used in conventional dye diffusion thermal transfer processes. See, for example, Advanced Printing of Conference Summaries, SPSE's 43rd Annual Conference, May 20–25, 1990, pp 266–268, SPSE, Springfield, Va., D. J. Harrison, *Thermal Dye Transfer Hard Copy Chemistry and Technology,* Eastman Kodak Company, Rochester, N.Y.

The heat-developable diffusion transfer image-recording materials of the present invention include those wherein the photosensitive silver halide emulsion layer(s) or the thermosensitive imaging layer(s) and the image-receiving layer are initially contained in separate elements which are brought into superposition subsequent to or prior to exposure. After development the two layers may be retained together in a single element, i.e., an integral negative-positive film unit or they can be peeled apart from one another. Alternatively, rather than being in separate elements, the photosensitive or thermosensitive layer(s) and the image-receiving layer may initially be in a single element wherein the negative and positive components are contained in a heat-developable laminate or otherwise retained together in an integral structure. After heat-development, the two layers may be retained together as a single element or they can be peeled apart from one another. Where the photosensitive silver halide emulsion or thermosensitive layer(s) and the image-receiving layer are retained together as an integral negative-positive film unit, a masking layer, e.g., titanium dioxide, is necessary to conceal the untransferred dye from the final image.

The photosensitive material of the present invention may be exposed by any of the methods used in the photographic art, e.g., a tungsten lamp, a mercury vapor lamp, a halogen lamp, fluorescent light, a xenon flash lamp or a light emitting diode including those which emit infrared radiation.

The photosensitive material of the present invention is heat-developed after imagewise exposure. This is generally accomplished by heating the material at a temperature in the range of 80° to 200° C., preferably in the range of 100° to 150° C., for a period of from 1 to 720 seconds, preferably 1.5 to 360 seconds. In order to transfer the released dye to the image-receiving sheet, both heat and pressure must be applied simultaneously. Thus, pressure can be applied simultaneously with the heat required for thermal development by using heated rollers or heated plates. Alternatively, heat and pressure can be applied subsequent to thermal development in order to transfer the released dye.

All methods of heating that can be employed in heat-developable photosensitive systems known in the art may be applied to the heat-developable photographic material of the present invention. Thus, for example, heating may be accomplished by using a hot plate, an iron, heated rollers or a hot drum.

For thermographic applications, heat is generally applied so as to obtain temperatures in the range of 80° to 200° C., preferably in the range of 100° to 150° C. The way in which the heat is applied or induced imagewise may be realized in a variety of ways, for example, by direct application of heat using a thermal printing head or thermal recording pen or by conduction from heated image-markings of an original using conventional thermographic copying techniques. Selective heating can be produced in the heat-sensitive element itself by the conversion of electromagnetic radiation into heat and preferably, the light source is a laser beam emitting source such as a gas laser or semiconductor laser diode. The use of a laser beam is not only well suited for recording in a scanning mode but by utilizing a highly concentrated beam, radiant energy can be concentrated in a small area so that it is possible to record at high speed and high density. Also, it is a convenient way to record data as a heat pattern in response to transmitted signals such as digitized information and a convenient way of preparing multicolor images by employing a plurality of laser beam sources that emit laser beams of different wavelengths.

If using an infrared emitting laser, the thermographic material also contains an infrared absorbing substance for converting infrared radiation into heat. Obviously, the infrared absorber should be in heat-conductive relationship with the thermosensitive materials, for example, in the same layer as the dye-providing material or in an adjacent layer. The infrared absorber may be an inorganic or organic compound, such as, a cyanine, merocyanine, squarylium or thiopyrylium dye and preferably, is substantially non-absorbing in the visible region of the electromagnetic spectrum.

Any image-receiving layer which has the capability of receiving the dye released as a result of thermal development may be used in the thermographic and photothermographic imaging materials of the present invention. Typical image-receiving layers which can be used are prepared by coating a support material with a suitable polymer for receiving the dye. Alternatively, certain polymers may be used as both the support and the dye receiving material.

The image-receiving layer is generally superposed on the photosensitive negative after exposure and the two are then heated simultaneously to develop the image and cause the dye to transfer. Alternatively, the negative may be exposed and then processed with heat, followed by superposing the image-receiving sheet on the exposed and developed photosensitive material and applying heat and pressure to transfer the dye. For thermographic imaging materials, the image-receiving layer is generally superposed on the thermosensitive imaging layer prior to heating and the two are then heated simultaneously to provide the image and cause the dye to transfer. For both photothermographic and thermographic imaging materials, the image-receiving layer is then generally peeled apart from the heat-sensitive layers.

Suitable polymers to be coated on the image-receiving support to receive dye include polyvinyl chloride (PVC), poly(methyl methacrylate), polyester, and polycarbonate. The preferred polymer is PVC.

The support materials which may be used for the image-receiving layer can be transparent or opaque. Examples of suitable supports are polymer films, such as, polyethylene terephthalate, polycarbonate, polystyrene, polyvinyl chloride, polyethylene, polypropylene and polyimide. The above supports can be made opaque by incorporating pigments therein, such as, titanium dioxide and calcium carbonate. Other supports include baryta paper, resin coated paper having paper laminated with pigmented thermoplastic resins, fabrics, glass, and metals.

Resin coated paper has been found to be a particularly useful support material for the image-receiving layer according to the present invention.

Additionally, the heat-developable image-recording materials of the present invention may include other materials heretofore suggested in the art but are not essential. These include, but are not limited to, antifoggants, antistatic materials, coating aids e.g, surfactants, activators and the like.

Also, the photosensitive elements may contain additional layers commonly used in the art, such as spacer layers, a layer of an antihalation dye, and/or a layer of a filter dye arranged between differentially color-sensitive emulsion layers. A protective layer may also be present in any of the image-recording materials of the present invention. The protective layer may contain a variety of additives commonly employed in the photographic art. Suitable additives include matting agents, colloidal silica, slip agents, organofluoro compounds, UV absorbers, accelerators, antioxidants, etc.

The present invention is illustrated by the following photothermographic and thermographic examples.

In the following Examples, the silver iodobromide dispersion is a 0.25 μm cubic unsensitized iodobromide (2% iodide) emulsion prepared by standard techniques known in the art. The silver salt oxidizer, thermal solvent, dye-providing material and reducing agents used in the Examples were added to the coating compositions as dispersions. The various dispersions were prepared by the specific procedures described below or by analogous procedures but using different reagents. The 1,2,4-triazole, glyoxal and succinaldehyde when added were added to the coating compositions as aqueous solutions.

(1) Silver Salt Dispersion 415 g of benzotriazole was added to 325 mL of concentrated ammonium hydroxide. To the resulting solution was added 450 g of gelatin and the mixture was diluted to a total volume of 6 liters with water. To this mixture, in the dark and at 40° C., was added a mixture prepared by combining 550 g of silver nitrate with 500 mL of concentrated ammonium hydroxide and diluted to a total volume of 2.1 liters with water. After the addition was complete, the material was washed using standard emulsion washing procedures and the pH adjusted to 6 and the pAg adjusted to 7.4.

(2) Thermal Solvent Dispersion 64 g of the thermal solvent designated TS-1, above, was dispersed in a mixture of 8.8 g of 10% aqueous polyvinylpyrrolidone, 10.8 g of 5% aqueous Alkanol XC (available from DuPont, Wilmington, Del.), and 160.4 g of water. The resulting mixture was ground in a ball mill for 7 hours. 100 g of water was introduced for washing purposes during the isolation of the dispersion.

(3) Dispersion of Dye-Providing Material 1.6 g of the dye-providing material of Formula (i) was dissolved in 5.0 g of ethyl acetate. 0.8 g of tricresylphosphate was added and the mixture was stirred and heated to 42° C. To the mixture at 42° C. was added a solution containing 21 g water, 4 g of 5% aqueous Alkanol XC and 8.5 g of 17.5% aqueous gelatin. The mixture was sonified with an ultrasonic probe for one minute in order to form a dispersion. The dispersion was stirred at 60° C. for 20 minutes to remove the ethyl acetate, followed by the addition of 14.1 g water.

(4) Reducing Agent Dispersion 3.0 g of 4-hydroxymethyl-4-methyl-1-phenyl-3-pyrazolidone (Dimezone-S) was added to 4.0 g of water and 3.0 g of 5% aqueous Alkanol XC. The resulting mixture was ground in a ball mill for 16 hours. The dispersion was diluted with water during isolation.

EXAMPLE 6

A heat-developable photosensitive material was prepared using the dispersions described above. A gelatin subcoated 4 mil polyester film (available from DuPont) was coated using a #30 Meyer Rod with an aqueous composition prepared in order to yield dry coating coverages of the respective components of layer 1 as follows:

| Layer 1 | |
|---|---|
| Gelatin | 2000 mg/m$^2$ |
| (Inert, deionized, derivatized bone gelatin, available from Rousselot, France) | |
| Dye-providing material | 0.5 mmol/m$^2$ |
| (Compound of Formula (i)) | |
| Zonyl FSN | 0.1% by wt. |
| (perfluoroalkyl polyethylene oxide non-ionic surfactant, available from DuPont, Wilmington, DE) | |
| Alkanol XC | 0.38% by wt. |

After air drying, layer 1 was overcoated with a composition (applied with a #30 Meyer Rod) prepared in order to yield coated coverages of the respective components of layer 2 as follows:

| Layer 2 | |
|---|---|
| Gelatin | 3000 mg/m$^2$ |
| Thermal Solvent (TS-1) | 1500 mg/m$^2$ |
| Reducing Agent (Dimezone S) | 4.0 mmol/m$^2$ |
| Silver Benzotriazole | 2.0 mmol/m$^2$ |
| Silver Iodobromide | 2.0 mmol/m$^2$ |
| Glyoxal | 100 mg/m$^2$ |
| 1,2,4-Triazole | 24 mmol/m$^2$ |
| Zonyl FSN | 0.1% by wt. |
| Alkanol XC | 0.04% by wt. |

The heat-developable photosensitive material was exposed to white light for $10^{-3}$ sec. An image-receiving sheet comprising a resin coated paper base overcoated with polyvinylchloride (12g/m$^2$) was superposed on the exposed, heat-developable photosensitive material and the assembly was processed at 120° C. for 180 sec at a pressure of 35 psi using a heated plate.

The photosensitive layer and dye-providing layer were peeled apart from the image-receiving layer after cooling below the melting point of the thermal solvent (104° C.), approximately 5 sec after processing. The maximum blue reflection density (Dmax) and the minimum density (Dmin) of the resulting image were measured using a reflection densitometer (MacBeth, model RD 514). The measured values are reported in Table 1.

TABLE 1

| | Dmax | Dmin |
|---|---|---|
| EXAMPLE 6 (Compound Formula (i)) | 0.59 | 0.26 |

EXAMPLE 7

Example 6 was repeated except that 0.25mmol/m$^2$ of the dye-providing material of Formula (ii) was used in place of the dye-providing material of Formula (i). The measured Dmax and Dmin values are reported in Table 2.

TABLE 2

| | Dmax | Dmin |
|---|---|---|
| EXAMPLE 7 (Compound Formula (ii)) | 0.51 | 0.39 |

EXAMPLE 8

A heat-developable photosensitive material was prepared, exposed and processed as described in Example 6 except that the components of layers 1 and 2 were coated to yield dry coating coverages as follows:

| | |
|---|---|
| Layer 1 | |
| Gelatin | 2000 mg/m$^2$ |
| Dye-providing material | 564 mg/m$^2$ |
| (Compound of Formula (xiii) as prepared in Example 2) | |
| Thermal Solvent (TS-1) | 1500 mg/m$^2$ |
| Zonyl FSN | 0.1% by wt. |
| Alkanol XC | 0.38% by wt. |
| Layer 2 | |
| Gelatin | 3000 mg/m$^2$ |
| Thermal Solvent (TS-1) | 1500 mg/m$^2$ |
| Dimezone S | 4.0 mmol/m$^2$ |
| Silver Benzotriazole | 1.0 mmol/m$^2$ |
| Silver Iodobromide | 2.0 mmol/m$^2$ |
| Glyoxal | 100 mg/m$^2$ |
| 1,2,4-Triazole | 24 mmol/m$^2$ |

-continued

| | |
|---|---|
| Benzotriazole | 4.4 mmol/m$^2$ |
| Zonyl FSN | 0.1% by wt. |
| Alkanol XC | 0.05% by wt. |

The measured Dmax and Dmin values are reported in Table 3.

EXAMPLE 9

Example 8 was repeated except that 564 mg/m$^2$ of the dye-providing material of Formula (xiv) having an average Mw of 26,841 was used in place of the compound of Formula (xiii). The measured Dmax and Dmin are reported in Table 3.

EXAMPLE 10

Example 9 was repeated except that instead of 564 mg/m$^2$, 846 mg/m$_2$ of the dye-providing material used in Example 9 was present and there was no glyoxal in layer 2. The measured Dmax and Dmin are reported in Table 3.

TABLE 3

| | Dmax | Dmin |
|---|---|---|
| EXAMPLE 8 (Compound Formula (xiii)) | 0.78 | 0.63 |
| EXAMPLE 9 (Compound Formula (xiv(a)) | 0.62 | 0.31 |
| EXAMPLE 10 (Compound Formula (xiv(b)) | 0.70 | 0.38 |

EXAMPLE 11

Three 2-layer heat-developable thermographic imaging materials were prepared as in Example 6 except that the photosensitive silver iodobromide and the reducing agent were left out and the dye-providing materials of Formulae (i), (ii), and (iii), respectively were used. The materials were imaged by heating; there was no exposure to light. The coated coverages of the respective components of layer 1 and layer 2 were as follows:

| | |
|---|---|
| **Layer 1** | |
| Gelatin | 2000 mg/m$^2$ |
| Dye-providing compounds | 0.5 mmol/m$^2$ |
| Thermal Solvent (TS-1) | 1500 mg/m$^2$ |
| Zonyl FSN | 0.1% by wt. |
| **Layer 2** | |
| Gelatin | 3000 mg/m$^2$ |
| Thermal Solvent (TS-1) | 3000 mg/m$^2$ |
| Silver Benzotriazole | 2.0 mmol/m$^2$ |
| Succinaldehyde | 100 mg/m$^2$ |
| 1,2,4-Triazole | 12.0 mmol/m$^2$ |
| Zonyl FSN | 0.1% by wt. |

The imaging material which employed the dye-providing material of Formula (iii) did not contain any thermal solvent in layer 1.

The image-receiving sheets were prepared as in Example 6. The image-receiving sheets were superposed on the respective heat-developable materials and each was processed at 120° C. for 180 sec. at a pressure of 35 psi by using heated plates. The maximum optical reflection density was measured for each material and they are reported in Table 4.

EXAMPLE 12

Two additional 2-layer heat-developable thermographic imaging materials were prepared and imaged as in Example 11 using the dye-providing compounds of Formulae iv and v. The coated coverages of the respective components of layers 1 and 2 were as follows:

| | |
|---|---|
| **Layer 1** | |
| Gelatin | 2000 mg/m$^2$ |
| Dye-providing compound | 0.5 mmol/m$^2$ |
| Thermal Solvent (TS-1) | 2000 mg/m$^2$ |
| **Layer 2** | |
| Gelatin | 1000 mg/m$^2$ |
| Thermal Solvent (TS-1) | 1000 mg/m$^2$ |
| Succinaldehyde | 60 mg/m$^2$ |
| Silver Benzotriazole | 2.0 mmol/m$^2$ |

The measured Dmax values are reported in Table 4.

TABLE 4

| DYE-PROVIDING MATERIAL | Dmax |
|---|---|
| Compound of Formula (i) | 1.08 |
| Compound of Formula (ii) | 1.17 |
| Compound of Formula (iii) | 0.70 |
| Compound of Formula (iv) | 0.73 |
| Compound of Formula (v) | 0.82 |

It is noted that the measured Dmin for examples 11 and 12 was that of the base material, 0.05.

Examples 6–12 demonstrate that the dye-providing compounds according to the present invention are useful in providing color images in heat-developable photographic and thermographic imaging systems.

The heat-developable materials prepared and processed in Examples 6–12 were processed base-free, i.e., they did not contain any added base or base-precursor and they were processed water-free, i.e., no water was added to aid in development or transfer. It is recognized what while the auxiliary ligand, 1,2,4-triazole, used in the examples may be classified as a weak base, it would not be considered to be a base or base-precursor as those terms are used in Japanese Kokai No. 59-180548. However, as stated earlier, the dye-providing compounds of the present invention may also be used in heat-developable imaging materials containing a base or base-precursor such as disclosed in the aforementioned Japanese Kokai No. 59–180548.

Since certain changes may be made in the above subject matter without departing from the spirit and scope of the invention herein involved, it is intended that all matter contained in the above description and the accompanying examples be interpreted as illustrative and not in any limiting sense.

We claim:

1. A compound represented by the formula:

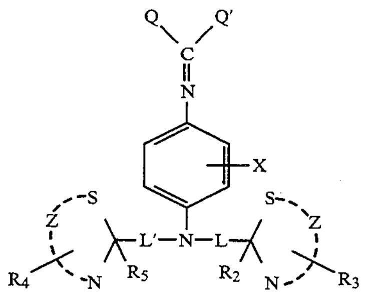

wherein:

Q, Q' and C taken together represent a dye forming coupler moiety wherein C is the coupling carbon of said coupler moiety;

X is selected from hydrogen, branched or unbranched alkyl, substituted alkyl, alkoxy, aryl, alkaryl, carboxy, amido, sulfamyl, sulfonamido, halo, nitro, and cyano;

$R_2$ and $R_5$, the same or different, represent hydrogen, a monovalent organic radical or together with L or L' represent the atoms necessary to complete a spiro union with one of the cyclic 1,2-sulfur-nitrogen moieties, or $R_2$ together with $R_5$ represents the atoms necessary to complete a 5, 6 or 7-membered heterocyclic ring with L', N and L;

$R_3$ and $R_4$, the same or different, are selected from the group consisting of: hydrogen, alkyl, aralkyl, alkaryl, and a polymer residue represented by the formula

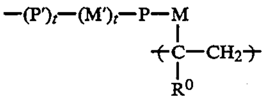

wherein $R^0$ represents hydrogen or lower alkyl containing 1 to 6 carbon atoms; M and M', the same or different, each represent a divalent linking group selected from the group consisting of

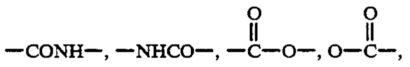

$-SO_2NH-$, and $-NH-CO-NH-$;

P and P', the same or different, each represent a divalent hydrocarbon group containing at least two carbon atoms; and t is 0 or 1;

L and L' represent divalent organic linking groups, the same or different, each containing at least two carbon atoms, provided that when one of L and L' contains 2 carbon atoms, the other contains at least 3 carbon atoms; and, Z and Z', the same or different, represent the carbon atoms necessary to complete an unsubstituted or substituted 5- or 6-membered heterocyclic ring system.

2. A compound according to claim 1 wherein said dye-forming coupler moiety is represented by

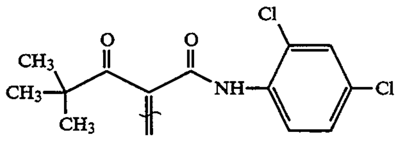

3. A compound according to claim 1 wherein said dye-forming coupler moiety is represented by

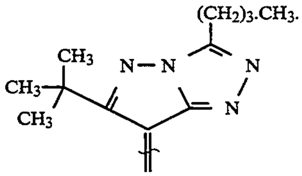

4. A compound according to claim 1 wherein said dye-forming coupler moiety is represented by

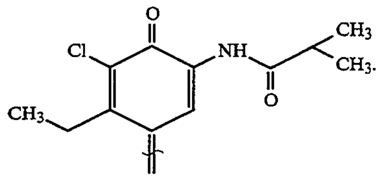

5. A compound according to claim 1 wherein said X is positioned ortho to the coupling nitrogen.

6. A compound according to claim 1 wherein said L and L', the same or different, each represent alkylene.

7. A compound according to claim 1 wherein Z and Z' are the same and represent the atoms necessary to complete a thiazolidine or benzothiazolidine moiety.

8. A compound according to claim 1 wherein said $R_3$ and $R_4$, the same or different, are each substituted on the respective N atoms of said thiazolidine or benzothiazolidine moieties.

9. A compound according to claim 1 represented by

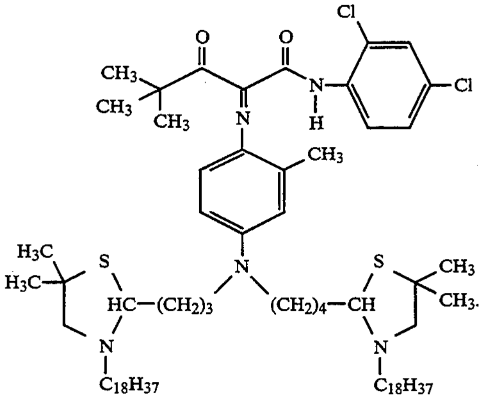

10. A compound according to claim 1 represented by

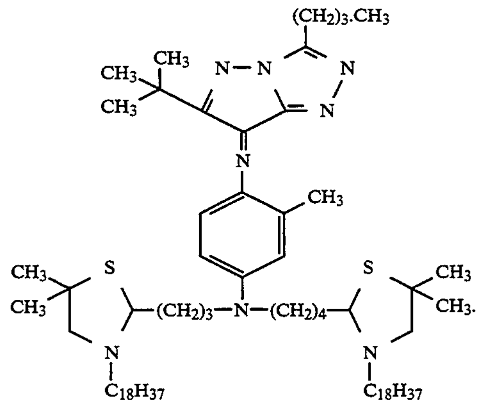

11. A compound according to claim 1 represented by

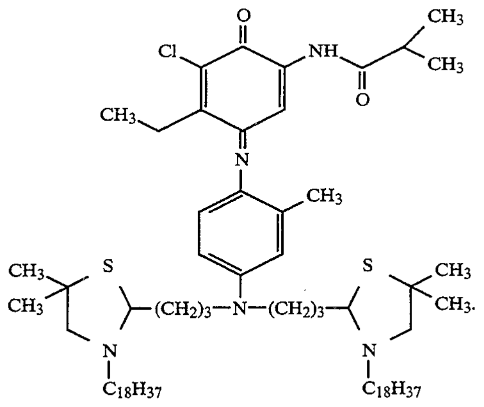
12. A compound according to claim 1 represented by
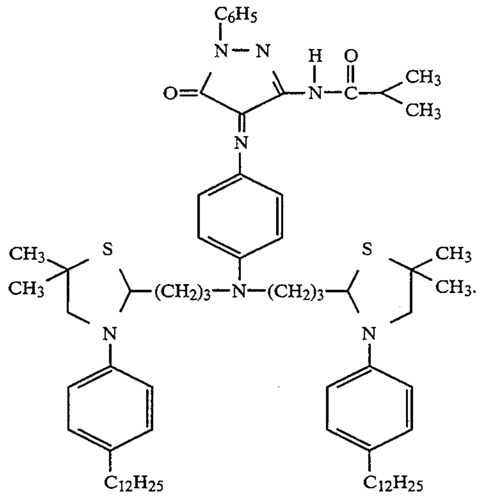
* * * * *